(12) United States Patent
Barker

(10) Patent No.: US 9,610,434 B2
(45) Date of Patent: Apr. 4, 2017

(54) SYSTEM AND METHOD FOR MAKING AND USING A LEAD INTRODUCER FOR AN IMPLANTABLE ELECTRICAL STIMULATION SYSTEM

(71) Applicant: BOSTON SCIENTIFIC NEUROMODULATION CORPORATION, Valencia, CA (US)

(72) Inventor: John Michael Barker, Ventura, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 322 days.

(21) Appl. No.: 14/193,682

(22) Filed: Feb. 28, 2014

(65) Prior Publication Data

US 2014/0276927 A1   Sep. 18, 2014

Related U.S. Application Data

(60) Provisional application No. 61/780,318, filed on Mar. 13, 2013.

(51) Int. Cl.
*A61N 1/05* (2006.01)
*A61B 17/34* (2006.01)
(Continued)

(52) U.S. Cl.
CPC ............ *A61N 1/05* (2013.01); *A61B 17/3468* (2013.01); *A61M 25/0668* (2013.01); *A61N 1/056* (2013.01); *A61M 29/00* (2013.01)

(58) Field of Classification Search
CPC .......... A61B 17/3468; A61M 25/0668; A61M 29/00
See application file for complete search history.

(56) References Cited

U.S. PATENT DOCUMENTS 3,330,278 A   7/1967   Santomieri
3,359,978 A   12/1967  Smith
(Continued)

FOREIGN PATENT DOCUMENTS

EP   2008686     12/2008
WO   03011361    2/2003

OTHER PUBLICATIONS

International Search Report and Written Opinion for PCT/US2014/019621 mailed Jun. 3, 2014.
(Continued)

*Primary Examiner* — Julie A Szpira
(74) *Attorney, Agent, or Firm* — Lowe Graham Jones PLLC; Bruce E. Black

(57) ABSTRACT

A lead introducer includes an insertion-needle assembly configured for receiving an electrical stimulation lead, and a splittable member that defines a lumen configured for receiving a portion of the insertion-needle assembly. The splittable member includes at least two pull-apart tabs disposed on a proximal hub of the splittable member and at least one splittable region extending along at least a portion of a longitudinal length of the splittable member from between the pull-apart tabs. The at least one splittable region is configured for separating when the pull-apart tabs are pulled apart from one another in directions approximately orthogonal to the splittable member. A lead-stabilization feature is configured for receiving, and temporarily retaining, a portion of an electrical stimulation lead extending outward from the splittable member such that the electrical stimulation lead does not move relative to the splittable member when the electrical stimulation lead is received by the lead-stabilization feature.

19 Claims, 13 Drawing Sheets

(51) Int. Cl.
*A61M 25/06* (2006.01)
*A61M 29/00* (2006.01)

(56) References Cited

U.S. PATENT DOCUMENTS

| | | | |
|---|---|---|---|
| 3,568,660 A | 3/1971 | Crites et al. | |
| 3,677,243 A | 7/1972 | Nerz | |
| 4,355,646 A | 10/1982 | Kallok et al. | |
| 4,449,973 A | 5/1984 | Luther | |
| RE31,855 E | 3/1985 | Osborne | |
| 4,512,351 A | 4/1985 | Pohndorf | |
| 4,608,986 A | 9/1986 | Beranek et al. | |
| 4,644,957 A * | 2/1987 | Ricciardelli | A61B 5/4362 600/372 |
| 4,808,157 A | 2/1989 | Coombs | |
| 5,125,904 A | 6/1992 | Lee | |
| 5,320,602 A | 6/1994 | Karpiel | |
| 5,380,290 A | 1/1995 | Makower et al. | |
| 5,409,469 A | 4/1995 | Schaerf | |
| 5,441,504 A | 8/1995 | Pohndorf et al. | |
| 5,713,867 A | 2/1998 | Morris | |
| 5,741,233 A | 4/1998 | Riddle et al. | |
| 5,752,937 A | 5/1998 | Otten et al. | |
| 5,755,693 A | 5/1998 | Walker et al. | |
| 5,931,863 A | 8/1999 | Griffin, III et al. | |
| 6,080,141 A | 6/2000 | Castro et al. | |
| 6,181,969 B1 | 1/2001 | Gord | |
| 6,251,119 B1 | 6/2001 | Addis | |
| 6,358,460 B1 | 3/2002 | Hunt, Jr. et al. | |
| 6,454,744 B1 | 9/2002 | Spohn et al. | |
| 6,494,860 B2 | 12/2002 | Rocamora et al. | |
| 6,516,227 B1 | 2/2003 | Meadows et al. | |
| 6,582,390 B1 | 6/2003 | Sanderson | |
| 6,609,029 B1 | 8/2003 | Mann et al. | |
| 6,609,032 B1 | 8/2003 | Woods et al. | |
| 6,641,564 B1 | 11/2003 | Kraus | |
| 6,645,178 B1 | 11/2003 | Junker et al. | |
| 6,712,791 B2 | 3/2004 | Lui et al. | |
| 6,741,892 B1 | 5/2004 | Meadows et al. | |
| 6,749,600 B1 | 6/2004 | Levy | |
| 6,758,854 B1 | 7/2004 | Butler et al. | |
| 6,869,416 B2 | 3/2005 | Windheuser et al. | |
| 6,939,327 B2 | 9/2005 | Hall et al. | |
| 7,001,396 B2 | 2/2006 | Glazier et al. | |
| 7,014,626 B2 | 3/2006 | Sanderson | |
| 7,101,353 B2 | 9/2006 | Lui et al. | |
| 7,192,433 B2 | 3/2007 | Osypka et al. | |
| 7,244,150 B1 | 7/2007 | Brase et al. | |
| 7,524,305 B2 | 4/2009 | Moyer | |
| 7,672,734 B2 | 3/2010 | Anderson et al. | |
| 7,744,571 B2 | 6/2010 | Fisher et al. | |
| 7,761,165 B1 | 7/2010 | He et al. | |
| 7,887,733 B2 | 2/2011 | Moyer | |
| 7,909,798 B2 | 3/2011 | Osypka | |
| 7,938,806 B2 | 5/2011 | Fisher et al. | |
| 7,941,227 B2 | 5/2011 | Barker | |
| 7,949,395 B2 | 5/2011 | Kuzma | |
| 7,985,232 B2 | 7/2011 | Potter et al. | |
| 7,993,305 B2 | 8/2011 | Ye et al. | |
| 8,043,263 B2 | 10/2011 | Helgeson et al. | |
| 8,105,287 B2 | 1/2012 | Fisher et al. | |
| 8,105,315 B2 | 1/2012 | Johnson et al. | |
| 8,112,159 B2 | 2/2012 | Harris et al. | |
| 8,147,456 B2 | 4/2012 | Fisher et al. | |
| 8,224,450 B2 | 7/2012 | Brase | |
| 8,273,059 B2 | 9/2012 | Nardeo et al. | |
| 8,348,899 B2 | 1/2013 | Chesnin et al. | |
| 8,377,006 B2 | 2/2013 | Tal et al. | |
| 8,382,715 B2 | 2/2013 | Nardeo et al. | |
| 2002/0111617 A1 | 8/2002 | Cosman et al. | |
| 2004/0054388 A1* | 3/2004 | Osypka | A61N 1/056 607/116 |
| 2004/0059392 A1 | 3/2004 | Parramon et al. | |
| 2005/0021119 A1 | 1/2005 | Sage et al. | |
| 2005/0055027 A1 | 3/2005 | Yeung et al. | |
| 2005/0107861 A1 | 5/2005 | Harris et al. | |
| 2005/0113860 A1 | 5/2005 | Keidar | |
| 2005/0165465 A1 | 7/2005 | Pianca et al. | |
| 2006/0122676 A1* | 6/2006 | Ko | A61M 25/0668 607/116 |
| 2006/0253181 A1* | 11/2006 | Schulman | A61N 1/0551 607/116 |
| 2007/0150036 A1 | 6/2007 | Anderson | |
| 2007/0219595 A1 | 9/2007 | He | |
| 2007/0239243 A1 | 10/2007 | Moffitt et al. | |
| 2008/0300538 A1 | 12/2008 | Schweikert et al. | |
| 2009/0248111 A1 | 10/2009 | Pianca et al. | |
| 2009/0254019 A1 | 10/2009 | Gehl et al. | |
| 2009/0259283 A1 | 10/2009 | Brandt | |
| 2011/0054402 A1 | 3/2011 | Tanabe et al. | |
| 2011/0218549 A1 | 9/2011 | Barker | |
| 2011/0224680 A1* | 9/2011 | Barker | A61B 17/3468 606/129 |
| 2011/0224681 A1 | 9/2011 | McDonald | |
| 2011/0230893 A1 | 9/2011 | Barker | |
| 2012/0323254 A1 | 12/2012 | Bonde et al. | |
| 2013/0053851 A1 | 2/2013 | Schmitz et al. | |
| 2014/0039586 A1 | 2/2014 | Barker et al. | |
| 2014/0073926 A1 | 3/2014 | Rajendran et al. | |
| 2014/0276927 A1 | 9/2014 | Barker | |
| 2015/0073431 A1 | 3/2015 | Barker | |
| 2015/0073432 A1 | 3/2015 | Barker | |

OTHER PUBLICATIONS

U.S. Appl. No. 62/153,844, filed Apr. 28, 2015.
U.S. Appl. No. 14/622,210, filed Feb. 13, 2015.

* cited by examiner

SYSTEM AND METHOD FOR MAKING AND USING A LEAD INTRODUCER FOR AN IMPLANTABLE ELECTRICAL STIMULATION SYSTEM

CROSS-REFERENCE TO RELATED APPLICATIONS

This application claims the benefit under 35 U.S.C. §119 (e) of U.S. Provisional Patent Application Ser. No. 61/780,318 filed Mar. 13, 2013, which is incorporated herein by reference.

FIELD

The present invention is directed to the area of implantable electrical stimulation systems and methods of making and using the systems. The present invention is also directed to a lead introducer for facilitating insertion of leads of implantable electrical stimulation systems into patients, as well as methods of making and using the leads, introducers, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a lead introducer includes an insertion-needle assembly configured and arranged for receiving an electrical stimulation lead. The insertion-needle assembly has a proximal end, a distal end, and a longitudinal length extending from the proximal end to the distal end. The insertion-needle assembly includes at least one proximal hub disposed at the proximal end. A splittable member has a proximal end, a distal end, and a longitudinal length extending from the proximal end to the distal end. The splittable member includes a proximal hub disposed at the proximal end. The splittable member defines a lumen configured and arranged for receiving at least a portion of the insertion-needle assembly. The splittable member includes at least two pull-apart tabs disposed on the proximal hub of the splittable member and at least one splittable region extending along at least a portion of the longitudinal length of the splittable member from between the at least two pull-apart tabs. The at least one splittable region is configured and arranged for separating when the at least two pull-apart tabs are pulled apart from one another in directions approximately orthogonal to the splittable member. A lead-stabilization feature is configured and arranged for receiving, and temporarily retaining, a portion of an electrical stimulation lead extending outward from the splittable member such that the electrical stimulation lead does not move relative to the splittable member when the electrical stimulation lead is received by the lead-stabilization feature.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to a lead introducer for facilitating insertion of leads of implantable electrical stimulation systems into patients, as well as methods of making and using the leads, introducers, and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 8,224,450; and U.S. Patent Applications Publication Nos. 2005/0165465, 2007/0150036; 2007/0219595; and 2007/0239243, all of which are incorporated by reference.

Figure 1:
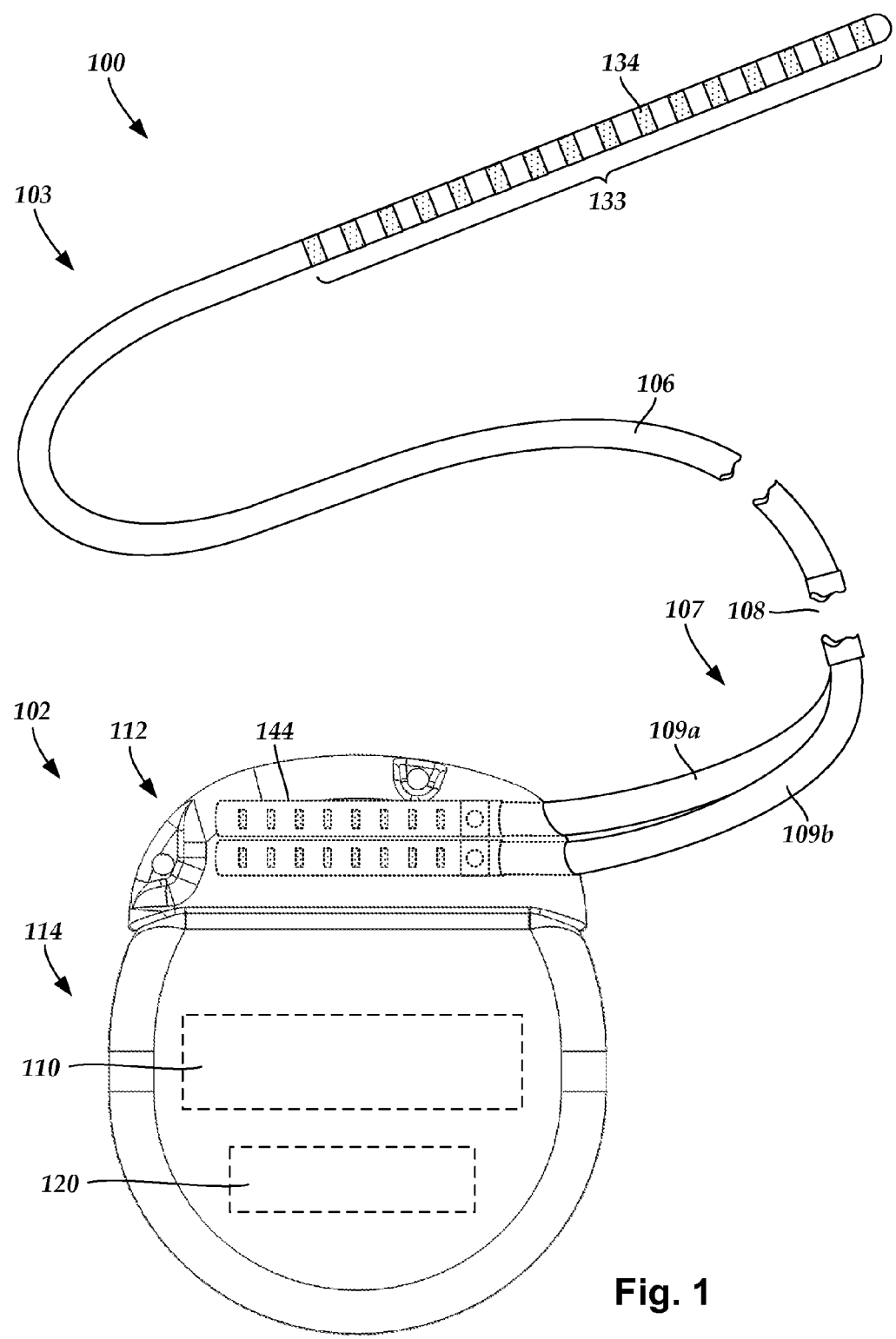
FIG. 1 is a schematic view of one embodiment of an electrical stimulation system, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes one or more lead bodies 106, an array of electrodes 133, such as electrode 134, and an array of terminals (e.g., 210 in FIG. 2A-2B) disposed along the one or more lead bodies 106. In at least some embodiments, the lead is isodiametric along a longitudinal length of the lead body 106.

The lead 103 can be coupled to the control module 102 in any suitable manner. In at least some embodiments, the lead 103 couples directly to the control module 102. In at least some other embodiments, the lead 103 couples to the control module 102 via one or more intermediate devices (200 in FIGS. 2A-2B). For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 1, the electrical stimulation system 100 is shown having a splitter 107 configured and arranged for facilitating coupling of the lead 103 to the control module 102. The splitter 107 includes a splitter connector 108 configured to couple to a proximal end of the lead 103, and one or more splitter tails 109a and 109b configured and arranged to couple to the control module 102 (or another splitter, a lead extension, an adaptor, or the like).

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including one or more of the lead bodies 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium. The number of electrodes 134 in each array 133 may vary. For example, there can be two, four, six, eight, ten, twelve, fourteen, sixteen, or more electrodes 134. As will be recognized, other numbers of electrodes 134 may also be used.

The electrodes of the one or more lead bodies 106 are typically disposed in, or separated by, a non-conductive, biocompatible material such as, for example, silicone, polyurethane, polyetheretherketone ("PEEK"), epoxy, and the like or combinations thereof. The lead bodies 106 may be formed in the desired shape by any process including, for example, molding (including injection molding), casting, and the like. The non-conductive material typically extends from the distal end of the one or more lead bodies 106 to the proximal end of each of the one or more lead bodies 106.

Figure 2A:
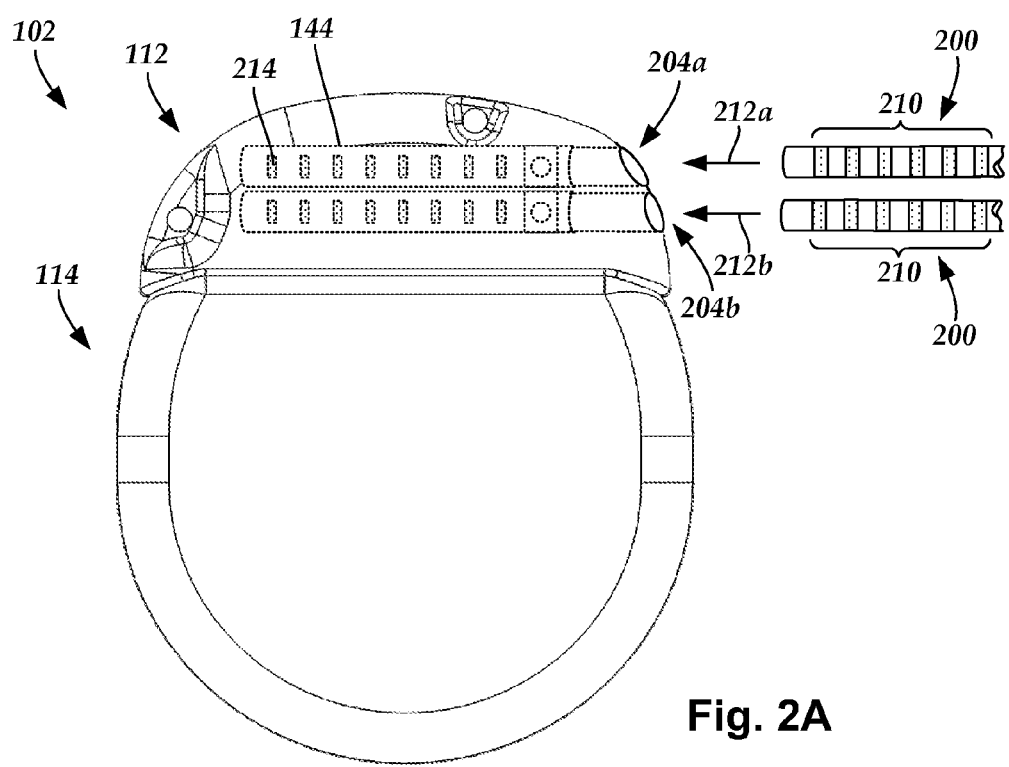
FIG. 2A is a schematic view of one embodiment of a proximal portion of a lead and a control module of an electrical stimulation system, according to the invention.
Figure 2B:
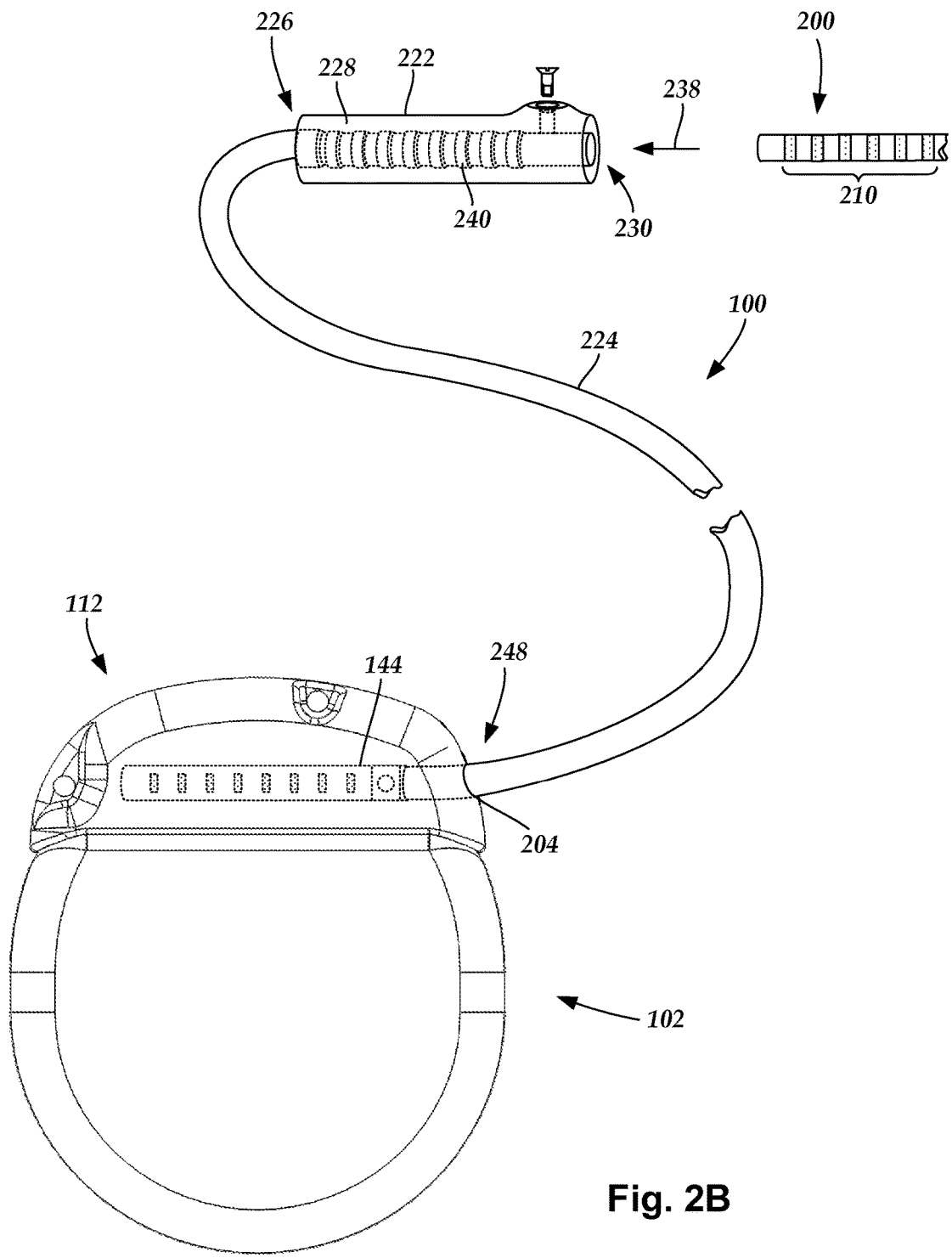
FIG. 2B is a schematic view of one embodiment of a proximal portion of a lead and a lead extension of an electrical stimulation system, according to the invention.

Terminals (e.g., 210 in FIGS. 2A-2B) are typically disposed along the proximal end of the one or more lead bodies 106 of the electrical stimulation system 100 (as well as any splitters, lead extensions, adaptors, or the like) for electrical connection to corresponding connector contacts (e.g., 214 in FIGS. 2A-2B; and 240 in FIG. 2B). The connector contacts are disposed in connectors (e.g., 144 in FIGS. 1-2B; and 222 in FIG. 2B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the lead body 106, for example, for inserting a stylet to facilitate placement of the lead body 106 within a body of a patient. Additionally, there may be one or more lumens (not shown) that open at, or near, the distal end of the lead body 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 2A is a schematic side view of one embodiment of a proximal end of one or more elongated devices 200 configured and arranged for coupling to one embodiment of the control module connector 144. The one or more elongated devices may include, for example, the lead body 106, one or more intermediate devices (e.g., the splitter 107 of FIG. 1, the lead extension 224 of FIG. 2B, an adaptor, or the like or combinations thereof), or a combination thereof.

The control module connector 144 defines at least one port into which a proximal end of the elongated device 200 can be inserted, as shown by directional arrows 212a and 212b. In FIG. 2A (and in other figures), the connector housing 112 is shown having two ports 204a and 204b. The connector housing 112 can define any suitable number of ports including, for example, one, two, three, four, five, six, seven, eight, or more ports.

The control module connector 144 also includes a plurality of connector contacts, such as connector contact 214, disposed within each port 204a and 204b. When the elongated device 200 is inserted into the ports 204a and 204b, the connector contacts 214 can be aligned with a plurality of terminals 210 disposed along the proximal end(s) of the elongated device(s) 200 to electrically couple the control module 102 to the electrodes (134 of FIG. 1) disposed at a distal end of the lead 103. Examples of connectors in control modules are found in, for example, U.S. Pat. Nos. 7,244,150 and 8,224,450, which are incorporated by reference.

FIG. 2B is a schematic side view of another embodiment of the electrical stimulation system 100. The electrical stimulation system 100 includes a lead extension 224 that is configured and arranged to couple one or more elongated devices 200 (e.g., the lead body 106, the splitter 107, an adaptor, another lead extension, or the like or combinations thereof) to the control module 102. In FIG. 2B, the lead extension 224 is shown coupled to a single port 204 defined in the control module connector 144. Additionally, the lead extension 224 is shown configured and arranged to couple to a single elongated device 200. In alternate embodiments, the lead extension 224 is configured and arranged to couple to multiple ports 204 defined in the control module connector 144, or to receive multiple elongated devices 200, or both.

A lead extension connector 222 is disposed on the lead extension 224. In FIG. 2B, the lead extension connector 222 is shown disposed at a distal end 226 of the lead extension 224. The lead extension connector 222 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of electrically conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

Some conventional percutaneous implantation techniques involve inserting a lead introducer, such as an epidural needle, into a patient. In one implantation technique, once the lead introducer is inserted into the patient, a lead is inserted into the lead introducer. The lead introducer (with the lead inserted therein) is positioned at a target stimulation location. Once the lead introducer is positioned at the target stimulation location, the lead introducer is removed from the patient, leaving the lead in place. Typically, the lead introducer is removed from the patient by sliding the lead introducer off the proximal end of the lead.

Unfortunately, when a lead is not isodiametric, it may be difficult to slide the lead introducer off the proximal end portion of the lead. For example, when a proximal end portion of a lead body has a diameter that is larger than a distal end portion of the lead body, or when an oversized junction or adapter is disposed along the length of the lead body, the varying diameters along a longitudinal length of the lead may hinder, or even prevent, the lead introducer from sliding off the proximal end portion of the lead.

A lateral-release lead introducer ("lead introducer") uses a multi-element insertion needle that enables a lead to be laterally separated from the multi-element insertion needle. In at least some embodiments, the lead is laterally separated from the multi-element insertion needle without sliding the multi-element insertion needle off the proximal end portion of the lead. The lead laterally separates from the multi-element insertion needle by passing the lead through an open channel defined along a length of the multi-element insertion needle.

Optionally, the lead introducer further includes a splittable member that separates from the lead by splitting apart along a length of the splittable member. In at least some embodiments, during implantation of the lead the multi-element insertion needle is disposed in the splittable member during a lead-implantation procedure. Examples of lead introducers and splittable members are found in, for example, U.S. Patent Application Publication No. 2011/0224680, which is incorporated by reference.

Figure 3:
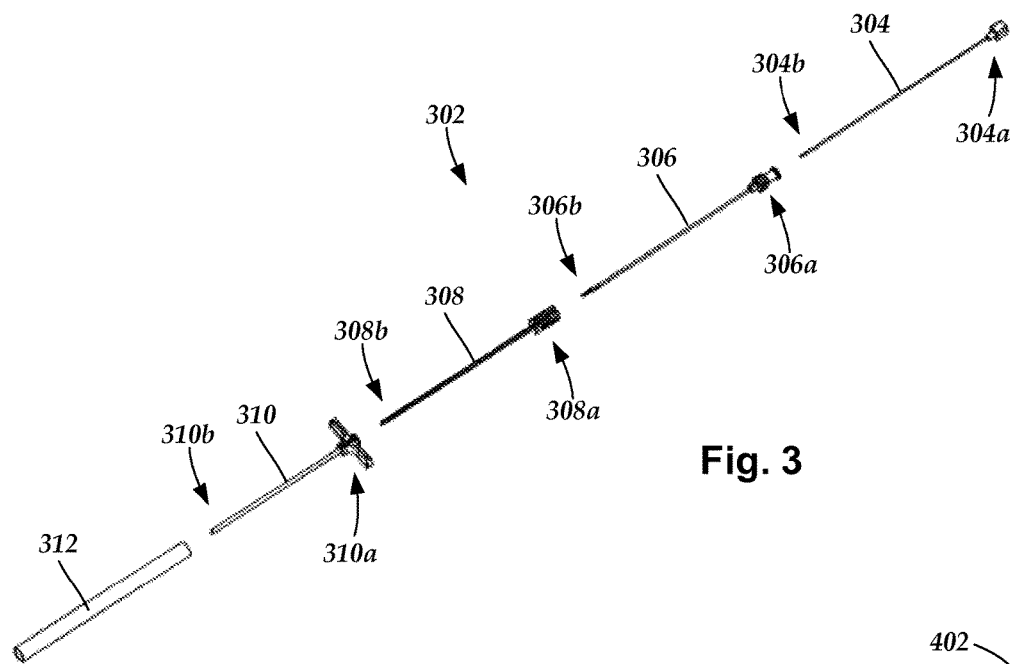
FIG. 3 is a schematic perspective exploded view of one embodiment of a lead introducer configured and arranged to facilitate implantation of an electrical stimulation system into a patient, according to the invention.

FIG. 3 is a schematic perspective exploded view of one embodiment of a lead introducer 302 configured and arranged to facilitate implantation of an electrical stimulation system into a patient. The lead introducer 302 of FIG. 3 includes an obturator 304, an inner insertion needle 306, an outer insertion needle 308, and a splittable member 310. The obturator 304 has a proximal hub 304a and a distal end 304b. The inner insertion needle 306 has a proximal hub 306a and a distal end 306b, and defines a lumen (504 in FIG. 5) extending between the proximal hub 306a and the distal end 306b. The outer insertion needle 308 has a proximal hub 308a and a distal end 308b, and defines an open channel (604 in FIG. 6) extending between the proximal hub 308a and the distal end 308b. The splittable member 310 has a proximal hub 310a and a distal end 310b, and defines a lumen (502 in FIG. 5) extending between the proximal hub 310a and the distal end 310b. Optionally, the lead introducer 302 may include a needle cover 312 to contain the lead introducer 302 prior to implantation.

Figure 4:
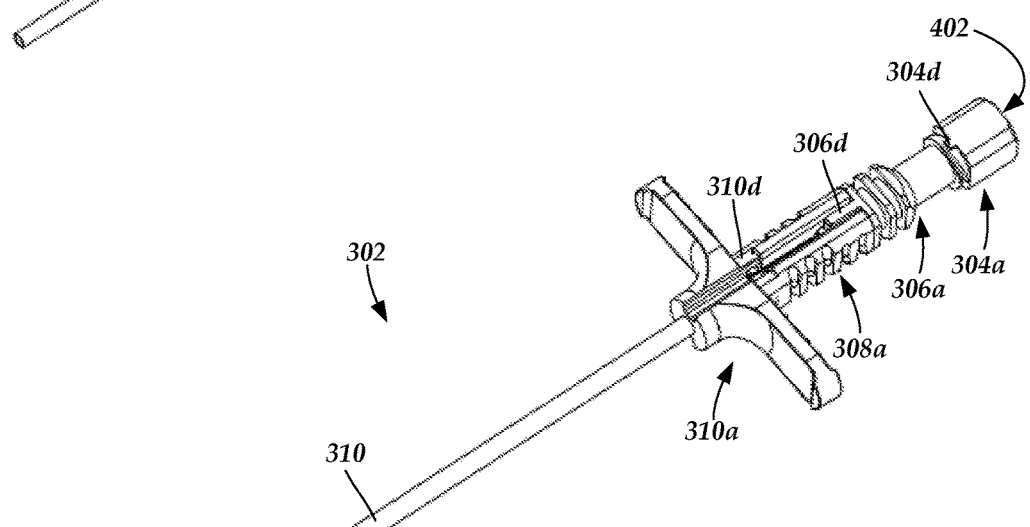
FIG. 4 is a schematic perspective view of one embodiment of the lead introducer of FIG. 3 with components of the lead introducer configured into a nested arrangement, according to the invention.

In at least some embodiments, the obturator 304, the inner insertion needle 306, the outer insertion needle 308, and the splittable member 310 are coupleable to one another such that the obturator 304, the inner insertion needle 306, the outer insertion needle 308, and the splittable member 310 form a nested arrangement. FIG. 4 is a schematic perspective view of one embodiment of the obturator 304 disposed in the lumen (504 in FIG. 5) of the inner insertion needle 306 which, in turn, is disposed in a channel (604 in FIG. 6) of the outer insertion needle 308 which, in turn is disposed in a lumen (502 in FIG. 5) of the splittable member 310.

In at least some embodiments, the obturator 304, the inner insertion needle 306, the outer insertion needle 308, and the splittable member 310 are configured such that, when the obturator 304, the inner insertion needle 306, the outer insertion needle 308, and the splittable member 310 are in a nested arrangement, the proximal hubs 304a, 306a, 308a, and 310a of the obturator 304, the inner insertion needle 306, the outer insertion needle 308, and the splittable member 310, respectively, align axially with one another.

It may be advantageous for the proximal hubs 304a, 306a, 308a, and 310a to be configured to prevent rotation relative to one another when the obturator 304, the inner insertion needle 306, the outer insertion needle 308, and the splittable member 310 are coupled together in a nested arrangement. Such a design may facilitate insertion of the lead introducer 302 into the patient by preventing unintended rotational movement of one or more components relative to the remaining components of the lead introducer 302. Also, such a design may ensure proper alignment of the components relative to one another to facilitate a lead-implantation procedure.

The proximal hubs 304a, 306a, 308a, and 310a may be prevented from rotating relative to one another when coupled to one another in any suitable manner. In at least some embodiments, the obturator 304, the inner insertion needle 306, the outer insertion needle 308, and the splittable member 310 are each keyed (e.g., a key formed along a first component fits into a keyhole formed in a second component to prevent rotation of the first component relative to the second component). In which case, the keys/keyholes may be incorporated along any suitable abutting portions of the obturator 304, the inner insertion needle 306, the outer insertion needle 308, and the splittable member 310.

In at least some embodiments, the keys/keyholes are formed in the proximal hubs 304a, 306a, 308a, and 310a. In FIG. 4, a key 304d is formed in the proximal hub 304a and is shown mated with a keyhole formed in the proximal hub 306a. FIG. 4 similarly shows a key 306d formed in the proximal hub 306a and mated with a keyhole formed in the proximal hub 308a; and a key 310d formed in the proximal hub 310a and mated with a keyhole formed in the proximal hub 308a.

In at least some embodiments, the outer insertion needle 308 is formed from a rigid material suitable for implantation, such as stainless steel. The inner insertion needle 306 may be formed from the same material as the outer insertion needle 308. In at least some embodiments, the inner insertion needle 306 is formed from a material that is more flexible than the outer insertion needle 308. In at least some embodiments, the outer insertion needle 308 is formed from a material that is more rigid than the splittable member 310. In at least some embodiments, the outer insertion needle 308 is formed from a material that is rigid enough to enable the outer insertion needle 308 to be used to guide (e.g., enable lateral steering) the splittable member 310 within a patient when the outer insertion needle 308 is disposed in the splittable member 310. In at least some embodiments, the lateral circumference of the outer insertion needle 308 is one of sixteen-gauge, fifteen-gauge, fourteen-gauge, thirteen-gauge, or twelve-gauge.

In at least some embodiments, the proximal hub 306a of the inner insertion needle includes a luer fitting 402 configured and arranged to receive a syringe. In at least some embodiments, fluid (e.g., saline solution, air, or the like) is introduced or removed through the luer fitting 402 to check for precise positioning of the lead introducer 302, for example, whether or not the epidural space has been entered.

Figure 5:
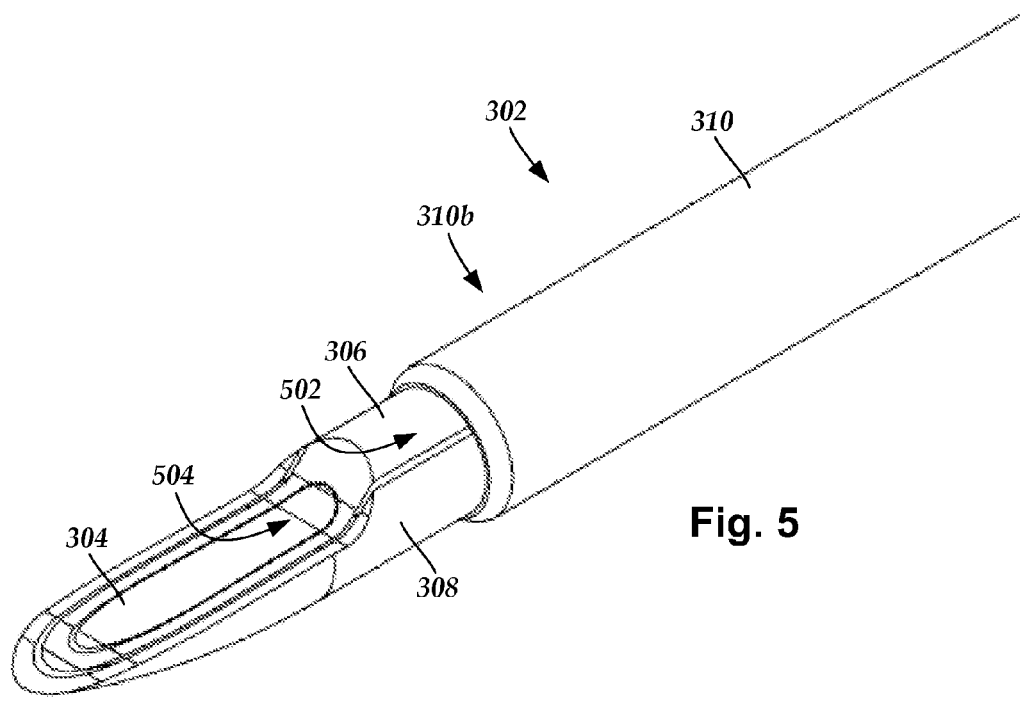
FIG. 5 is a schematic perspective close-up view of one embodiment of a distal end of the lead introducer of FIG. 4, according to the invention.

FIG. 5 is a schematic perspective close-up view of one embodiment of a distal end portion of the lead introducer 302 configured into a nested arrangement. In at least some embodiments, when the obturator 304, the inner insertion needle 306, the outer insertion needle 308, and the splittable member 310 are arranged into a nested arrangement, the distal ends 304b, 306b, and 308b of the obturator 304, the inner insertion needle 306, and the outer insertion needle 308, respectively, extend distally beyond the distal end 310b of the splittable member 310.

As shown in FIG. 5, the outer insertion needle 308 is disposed in a lumen 502 of the splittable member 310; the inner insertion needle 306 is disposed in a channel (604 in FIG. 6) of the outer insertion needle 308; and the obturator 304 is disposed in a lumen 504 defined along the inner insertion needle 306.

The distal end of the outer insertion needle 308 and the distal end of the inner insertion needle 306 are typically configured and arranged to pierce patient tissue. In at least some embodiments, the distal end 308b of the outer insertion needle 308 and the distal end 306b of the inner insertion needle 306 are flush with one another. Alternately, in at least some embodiments the distal end 306b of the inner insertion needle 306 is inset from the distal end 308b of the outer insertion needle 308. In at least some embodiments, the distal end 304b of the obturator 304 is flush with at least one of the distal end 306b of the inner insertion needle 306 or the distal end 308b of the outer insertion needle 308. In at least some embodiments, the distal end 304b of the obturator 304 includes a blunt tip to reduce or prevent coring of patient tissue during insertion of the lead introducer 302 into a patient.

The outer insertion needle 308 may be configured and arranged to receive a distal end portion of a lead when the inner insertion needle 306 is not disposed in the outer insertion needle 308. In other words, the outer insertion needle 308 is configured and arranged to sequentially receive the inner insertion needle 306 and the distal end portion of the lead.

Figure 6A:
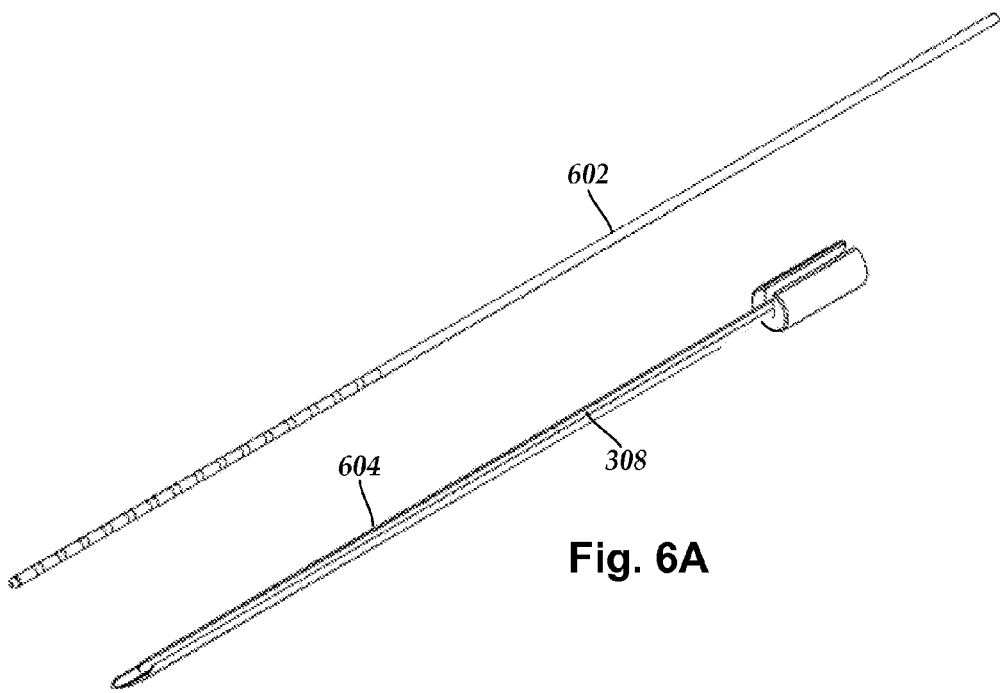
FIG. 6A is a schematic perspective view of one embodiment of a distal end portion of a lead and an outer insertion needle of the lead introducer of FIG. 3, the outer insertion needle defining an open channel extending along a length of the outer insertion needle, the open channel configured and arranged to receive the lead, according to the invention.

FIG. 6A is a schematic perspective view of one embodiment of a distal end portion of a lead 602 and the outer insertion needle 308 of the lead introducer 302. The outer insertion needle 308 defines an open channel 604 that extends substantially entirely along a length of the outer insertion needle 308 and that is configured and arranged to receive the distal end portion of the lead 602. In at least some embodiments, the open channel 604 extends along the proximal hub 308a of the outer insertion needle 308. In at least some embodiments, the open channel 604 extends along an entire longitudinal length of the of the outer insertion needle 308.

In some embodiments, the lead 602 has an isodiametric lead body. In other embodiments, the lead 602 has a non-isodiametric lead body. In at least some embodiments, the lead 602 includes one or more elements (e.g., a junction, adaptor, or the like) disposed along the length of the lead 602 which have a transverse cross-sectional shape or size that is different from at least one other portion of the lead 602. In at least some embodiments, the distal end portion of the lead 602 has a transverse cross-sectional shape that is similar to a transverse cross-sectional shape of the inner insertion needle 306. In at least some embodiments, the one or more elements having a different transverse cross-sectional shape or size are disposed along a proximal end portion of the lead 602.

In at least some embodiments, the lead 602 includes one or more elements having a transverse cross-sectional shape or size that is different from at least one other portion of the lead 602, while having a lead body that is isodiametric along the lead body between the plurality of electrodes and the one or more elements. In at least some embodiments, the lead 602 includes one or more elements having a transverse cross-sectional shape or size that is different from at least one other portion of the lead 602, while having a lead body that is isodiametric along the entire portion of the lead body distal to the one or more elements.

In at least some embodiments, the inner insertion needle 306 is configured and arranged to at least substantially fill the open channel 604 when the inner insertion needle 306 is disposed in the open channel 604. In at least some embodiments, the inner insertion needle 306 is configured and arranged for insertion into and out of the open channel 604 of the outer insertion needle 308 by sliding the inner insertion needle 306 axially along the open channel 604. In at least some embodiments, the open channel 604 has a width that is no less than a diameter of the inner insertion needle 306.

In at least some embodiments, the lead 602 is configured and arranged to at least substantially fill the open channel 604 when the lead 602 is disposed in the open channel 604. In at least some embodiments, the lead 602 is configured and arranged for insertion into and out of the open channel 604 of the outer insertion needle 308 by sliding the lead 602 axially along the open channel 604. In at least some embodiments, the open channel 604 has a width that is no less than a diameter of the lead 602. In at least some embodiments, the inner insertion needle 306 and the lead 602 have equal diameters.

In at least some embodiments, when the lead 602 is disposed in the open channel 604 and inserted at least partially into a patient, the lead 602 is separatable from the open channel 604 without moving the lead 602 axially relative to the outer insertion needle 308. In at least some embodiments, the lead 602 is removable from the open channel 604 by applying enough lateral force to at least one of the lead 602 or the outer insertion needle 308 to pass the lead 602 laterally out through the open channel 604. In at least some embodiments, the open channel 604 is configured and arranged such that, when the splittable member 310 is removed from the outer insertion needle 308, the lead 602 is configured and arranged to separate from the outer insertion needle 308 without applying lateral force to either the lead 602 or the outer insertion needle 308.

Figure 6B:
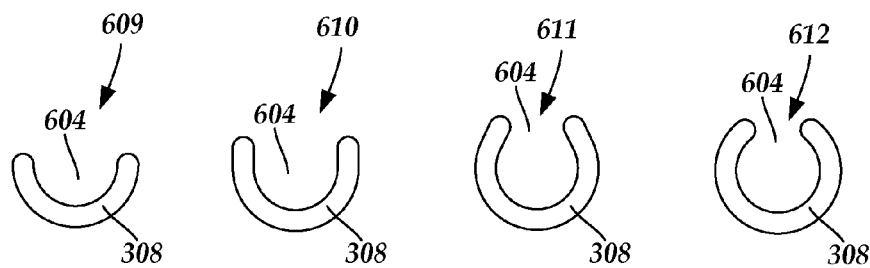
FIG. 6B is a schematic transverse cross-sectional view of several exemplary embodiments of the open channel of the outer insertion needle of FIG. 6A, according to the invention.

FIG. 6B shows schematic transverse cross-sectional views of several different exemplary embodiments of the open channel 604 of the outer insertion needle 308. In at least some embodiments, the portions of the outer insertion needle 308 along which the open channel 604 extends have a transverse cross-sectional shape that is at least substantially semi-circular-shaped 609, substantially U-shaped 610, substantially horseshoe-shaped 611, substantially C-shaped 612, or the like.

Figure 7:
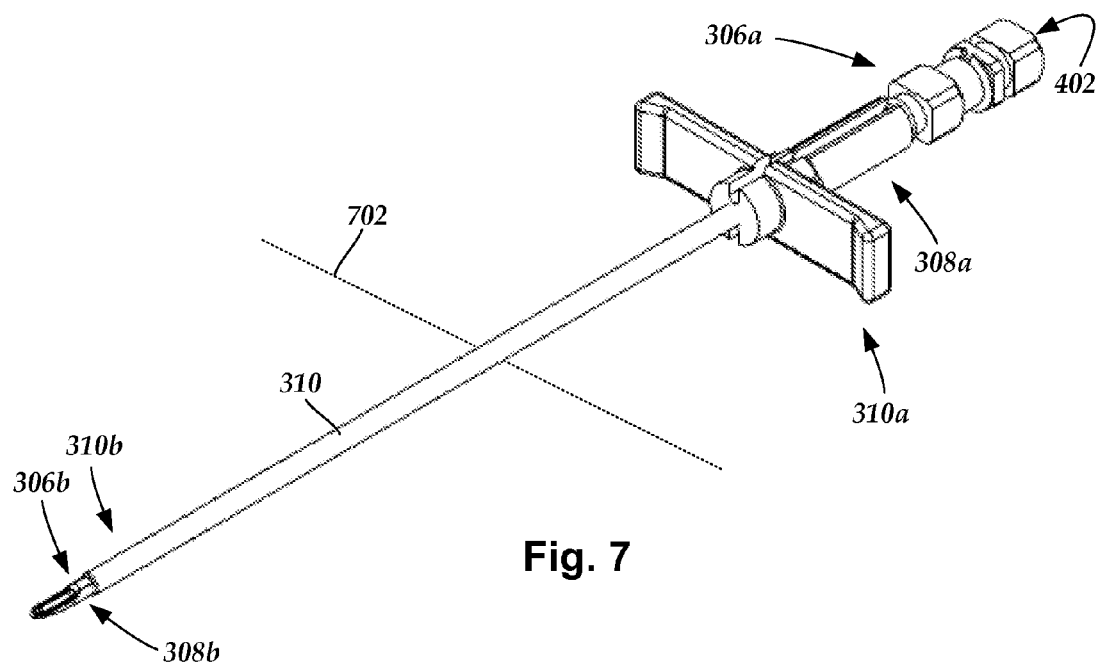
FIG. 7 is a schematic perspective view of one embodiment of the lead introducer of FIG. 4 partially inserted into a patient and an obturator removed from the lead introducer, according to the invention.

Turning to FIG. 7, the lead 602 may be inserted into a patient using the lead introducer 302. In at least some embodiments, a lead-implantation procedure includes forming the lead introducer 302 into a nested configuration (e.g., inserting the obturator 304 into the lumen 504 of the inner insertion needle 306; inserting the inner insertion needle 306 into the open channel 604 of the outer insertion needle 308; and inserting the outer insertion needle 308 into the lumen 502 of the splittable member 310).

It will be understood that the components of the lead introducer 302 can be assembled in any order. For example, the inner insertion needle 306 can be inserted into the open channel 604 of the outer insertion needle 308 either before or after the outer insertion needle 308 is inserted into the splittable member 310. In preferred embodiments, the lead introducer 302 is pre-assembled into a nested configuration prior to a lead-implantation procedure.

The assembled (e.g., nested) lead introducer 302 is inserted into a patient and guided in proximity to a target stimulation location (e.g., several vertebrae levels above or below the target stimulation location). Optionally, once the lead introducer 302 is in proximity to the target stimulation location, the obturator 304 is removed and fluid is introduced or removed through the luer fitting (402 in FIG. 4) of the inner insertion needle 306 to check for precise positioning of the lead introducer 302, for example, in an epidural space of the patient.

FIG. 7 is a schematic perspective view of one embodiment of the inner insertion needle 306 inserted into the open channel 604 of the outer insertion needle 308 which, in turn, is inserted into the splittable member 310. In FIG. 7, the distal ends of each of the inner insertion needle 306, the outer insertion needle 308, and the splittable member 310 are disposed in a patient, as shown by a dotted line 702. The obturator 304 has been removed to allow access to the luer fitting 402 for performing the optional loss of resistance test. It will be understood that the assembled lead introducer 302 can, alternately, be inserted into a patient and guided in proximity to a target stimulation location without using the obturator 304.

Figure 8:
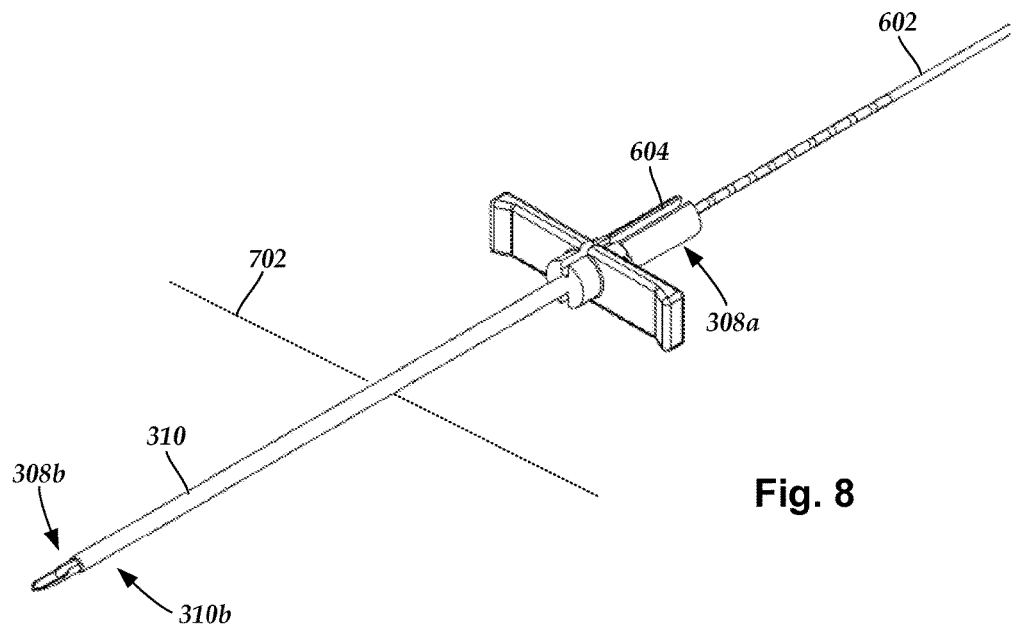
FIG. 8 is a schematic perspective view of one embodiment of the lead introducer of FIG. 7 partially inserted into a patient and an inner insertion needle removed from the lead introducer and replaced with the lead of FIG. 6A, according to the invention.

Turning to FIG. 8, once the lead introducer 302 is positioned in the epidural space in proximity to the target stimulation location, the inner insertion needle 306 may be removed from the open channel 604 of the outer insertion needle 308 and the distal end portion of the lead 602 may be inserted into the open channel 604 of the outer insertion needle 308.

FIG. 8 is a schematic perspective view of one embodiment of the distal end portion of the lead 602 partially inserted into the open channel 604 of the outer insertion needle 308 via the proximal hub 308a. Once the distal end portion of the lead 602 is inserted into the open channel 604 of the outer insertion needle 308, the positioning of the lead introducer 302 and the distal end portion of the lead 602 may be adjusted to place the distal end portion of the lead 602 within operational proximity to the target stimulation location.

It may be advantageous to place the lead 602 while the lead 602 is disposed in the outer insertion needle 308 and the splittable member 310. The outer insertion needle 308 and the splittable member 310 may provide the clinician with the ability to steer the lead introducer 302 by applying a lateral force of the lead introducer 302 to direct the trajectory of the lead 602. In at least some embodiments, the outer insertion needle 308 provides the rigidity needed for placing the distal end portion of the lead 602 within operational proximity to the target stimulation location. In at least some embodiments, the splittable member 310 lacks the rigidity necessary to provide such steering ability.

Figure 9:
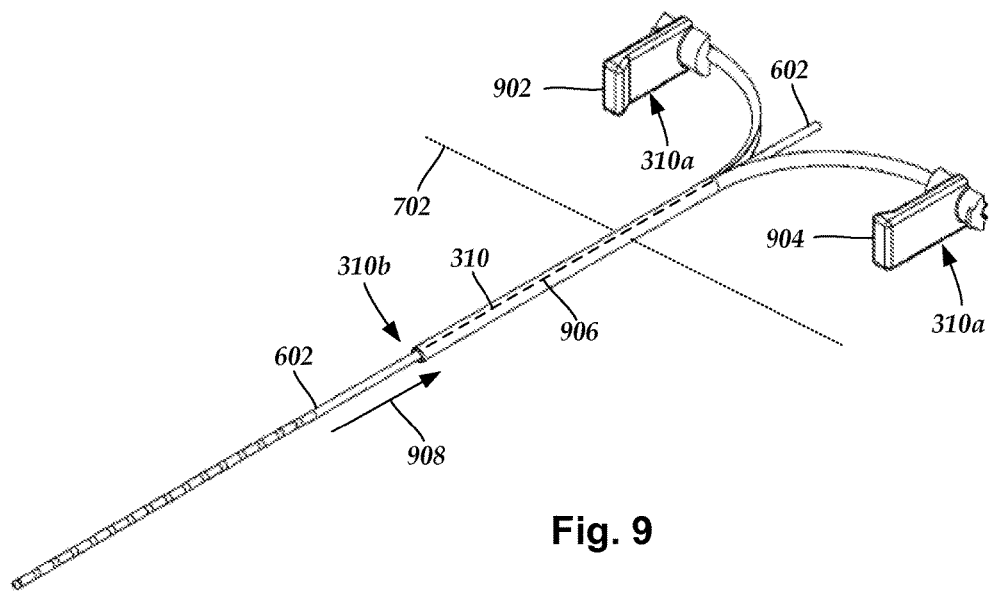
FIG. 9 is a schematic perspective view of one embodiment of the lead introducer of FIG. 8 partially inserted into a patient and a splittable member of the lead introducer being split apart to remove the splittable member from the lead of FIG. 8 while the lead remains inserted into the patient, according to the invention.

Turning to FIG. 9, once the distal end of the lead 602 has been placed in operational proximity to the target stimulation location, the outer insertion needle 308 and the splittable member 310 may be separated from the lead 602 and removed from the patient, leaving the lead behind in the patient. In at least some embodiments, the outer insertion needle 308 is separated from the lead 602 prior to the splittable member 310 being separated from the lead 602. Note that, in FIG. 9 the outer insertion needle 308 has already been removed from the lead 602. Removal of the outer insertion needle 308 is discussed in more detail with reference to FIGS. 11-17.

FIG. 9 is a schematic perspective view of one embodiment of the splittable member 310 being split apart to remove the splittable member 310 from the lead 602. Optionally, the proximal hub 310a of the splittable member 310 includes at least two pull-apart tabs 902 and 904 configured and arranged for facilitating separation of the splittable member 310.

In at least some embodiments, the splittable member 310 is formed from a flexible material suitable for implantation into the patient 702 including, for example, fluorinated ethylene propylene, polytetrafluoroethylene, high-density polyethylene, polyetheretherketone, and the like or combinations thereof. Additionally, one or more radiopaque materials may be added including, for example, barium sulfate and bismuth subcarbonate, and the like or combinations thereof to facilitate implantation of the introducer sheath through the use of one or more medical imaging techniques, such as fluoroscopy.

In at least some embodiments, the splittable member 310 includes one or more splittable regions 906 that form lines along a longitudinal length of the splittable member 310 along which the splittable member 310 preferentially separates when the tabs 902 and 904 are pulled apart from one another. The splittable regions 906 can be formed in any suitable manner including, for example, score lines, perforations, elongated regions of decreased thickness from surrounding regions, elongated regions of comparatively-weak material from surrounding regions, or the like or combinations thereof.

In at least some embodiments, the splittable regions 906 are formed along at least 25%, 50%, 75%, or 90% of the longitudinal length of the splittable member 310. In at least some embodiments, the splittable regions 906 are formed along the entire longitudinal length of the splittable member 310 between the at least two pull-apart tabs 902 and 904, including the proximal hub 310a. In at least some embodiments, when the at least two pull-apart tabs 902 and 904 are separated from one another, for example, by pulling each pull-apart tab away from the other pull-apart tab(s) in directions approximately orthogonal to the splittable member 310, the splittable member 310 separates along the one or more splittable regions 906.

In at least some embodiments, the splittable member 310 is separated into a plurality of longitudinal strips while pulling the splittable member 310 proximally along the lead 602. As the splittable member 310 splits apart, the distal end 310b of the splittable member 310 may move proximally along the lead 602 (as shown by arrow 908), with an increasing amount of the lead 602 extending through the distal end 310b of the splittable member 310. In at least some embodiments, an undersurface of the splittable member 310 includes a lubricious coating to facilitate the proximal movement of the splittable member 310.

Eventually, the splittable member 310 may be completely separated into two or more discrete longitudinal strips, thereby separating completely from the lead 602 and also from the patient. In at least some embodiments, the distal ends of the splittable member 310 may be extracted from the patient as the splittable member 310 is split apart. In at least some embodiments, the splittable member 310 may be split apart without causing the distal end portion of the lead 602 to move.

Once the lead 602 is positioned at the target stimulation location, the lead 602 may be coupled to a control module (e.g., 102 of FIG. 1) and implanted using well-known techniques, for example, using one or more using tunneling straws placed in passageways underneath patient skin with bores that are sized large enough to receive the lead 602. In at least some embodiments, the lead 602 may be coupled to a connector of a control module, as shown in FIGS. 1-2B. In other embodiments, the lead 602 may be coupled to one or more other devices, including an adaptor, a lead extension, an operating room cable, or the like or combinations thereof.

Figure 10:
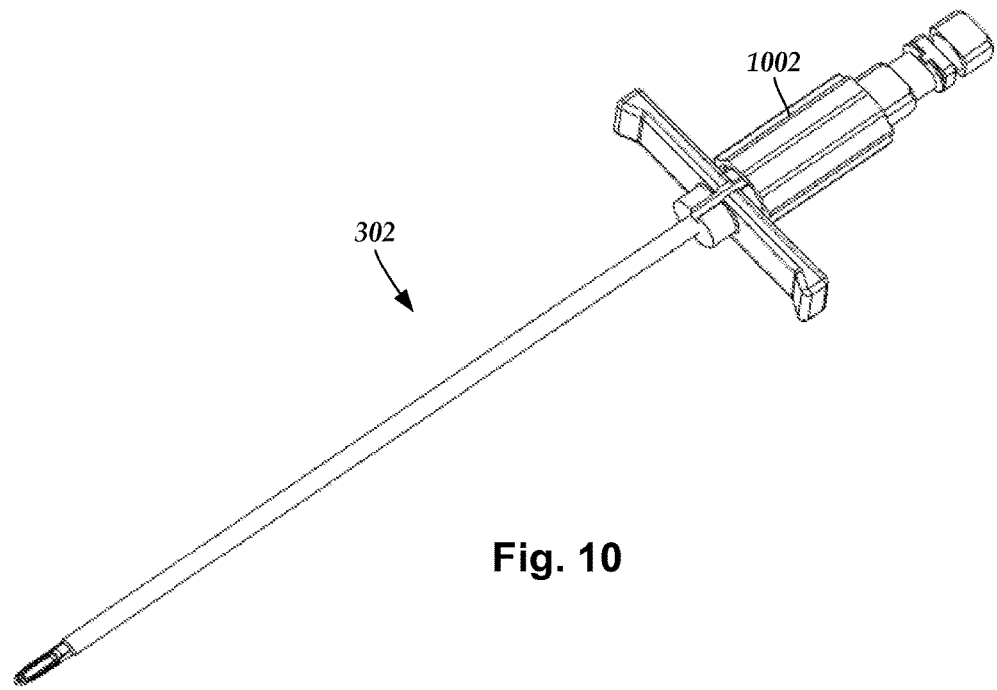
FIG. 10 is a schematic perspective view of one embodiment of a luer lock collar disposed over proximal hubs of components of the lead introducer of FIG. 4, the luer lock collar locking the components of the lead introducer in place relative to one another, according to the invention.

Turing to FIG. 10, a luer lock collar may, optionally, be disposed on the proximal hub 306a of the inner insertion needle 306 to lock the inner insertion needle 306, the outer insertion needle 308, and the splittable member 310 all together during insertion of the lead introducer 302 into the patient. FIG. 10 is a schematic perspective view of one embodiment of a luer lock collar 1002 disposed over the proximal hub 308a of the outer insertion needle 308. The luer lock collar 1002 is configured and arranged to lock the inner insertion needle 306, the outer insertion needle 308, and the splittable member 310 all together during insertion of the lead introducer 302 into the patient.

Figure 11:
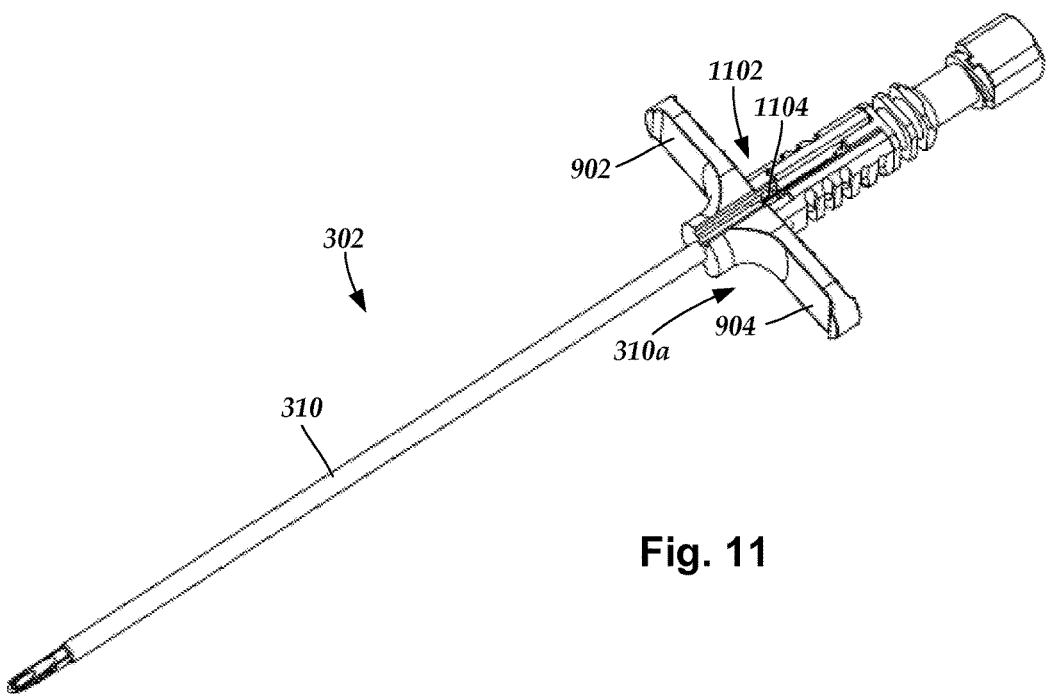
FIG. 11 is a schematic perspective view of a first embodiment of a lead-stabilization feature incorporated into the lead introducer of FIG. 4, the lead-stabilization feature formed as a notch in a proximal hub of a splittable member of the lead introducer, according to the invention.

Turning to FIG. 11, during removal of the outer insertion needle 308 from the lead 602, the outer insertion needle 308 may, in some instances, cause some amount of movement (e.g., axial movement) of the lead 602. For example, the outer insertion needle 308 may temporarily stick to one or more portions of the lead 602 and may drag the lead 602 until enough force is applied by a user to fully detach the lead 602 from the outer insertion needle 308. Such movement of the lead 602 may be undesired because the lead 602 may, at the time of removal of the outer insertion needle 308, be placed in operational proximity to the target stimulation location. In some instances, a medical practitioner may be able to prevent the lead 602 from being dragged with the outer insertion needle 308 by manually holding the lead 602 in position during removal of the outer insertion needle 308. Removal of the outer insertion needle 308, however, may be difficult to undertake while simultaneously holding the lead 602 in position.

In at least some embodiments, a lead-stabilization feature is usable to stabilize the lead 602 during removal of the outer insertion needle 308 during a lead-implantation procedure. In at least some embodiments, the lead-stabilization feature is configured and arranged to stabilize the lead 602 by receiving, and temporarily retaining, the portion of the lead 602 disposed within the splittable member 310 while the outer insertion needle 308 is removed from the patient. In at least some embodiments, the lead-stabilization feature is configured and arranged to temporarily retain a portion of the lead 602 such that the lead is prevented from moving relative to the splittable member 310.

In at least some embodiments, the lead-stabilization feature is configured and arranged to retain the portion of the lead 602 extending from the splittable member 310 such that the lead 602 the proximal hub 308a of the outer insertion needle 308 is unobstructed by the portion of the lead 602 extending from the splittable member 310. In at least some embodiments, the lead-stabilization feature is configured and arranged to retain the portion of the lead 602 extending from the splittable member 310 such that the portion of the lead 602 extending from the splittable member 310 is fully removed from the portion of the open channel 604 extending along the proximal hub 308a of the outer insertion needle 308.

In at least some embodiments, the lead-stabilization feature is configured and arranged to stabilized the lead 602 without requiring a medical practitioner to manually hold the lead 602 during removal of the outer insertion needle 308. In preferred embodiments, once the outer insertion needle 308 is fully removed from the lead 602 and the splittable member 310, the lead 602 may be removed from the lead-stabilization feature and the splittable member 310 may be removed from lead 602.

A lead-stabilization feature may be implemented in any suitable manner. In at least some embodiments, the lead-stabilization feature includes a notch configured to removably receive a portion of the lead 602 extending from the proximal hub 310a. FIG. 11 is a schematic perspective view of one embodiment of a lead-stabilization feature 1102 incorporated into the lead introducer 302. The lead-stabilization feature 1102 of FIG. 11 includes a notch 1104 defined in the proximal hub 310a of the splittable member 310.

The notch 1104 is configured and arranged to receive, and removably retain, a portion of the lead 602. In at least some embodiments, the notch 1104 is formed along an outer surface of the proximal hub 310a such that the notch 1104 opens to the lumen (502 in FIG. 5) of the splittable member 310. It may be advantageous for the notch 1104 to open to the lumen of the splittable member 310 so that, when a portion of the lead 602 is disposed in the lumen of the splittable member 310, a portion of the lead 602 extending from the lumen may be manually placed in the notch 1104 without disturbing the portion of the lead 602 disposed in the lumen of the splittable member 310.

In at least some embodiments, the notch 1104 is configured and arranged form an interference fit with the lead 602 when the lead 602 is receive by the notch 1104. In at least some embodiments, the notch 1104 has a diameter that is smaller than a diameter of the lead 602. In at least some embodiments, the notch 1104 has a diameter that is at least 5%, 10%, 15%, 20%, 25% smaller than a diameter of the lead 602. In at least some embodiments, the notch 1104 has a diameter that is no more than 25%, 20%, 15%, 10%, 5% smaller than a diameter of the lead 602.

In at least some embodiments, the notch 1104 is positioned along the proximal hub 310a such that at least one of the one or more splittable regions (906 in FIG. 9) extends across the notch 1104 with the notch 1104 opening up when the tabs 902 and 904 are separated from one another. In at least some embodiments, two tabs 902 and 904 are disposed on the proximal hub 310a such that the tabs 902 and 904 are positioned 180-degrees apart from each other along a circumference of the proximal hub 310a. In which case, in at least some embodiments the notch 1104 is disposed 90-degrees apart from each of the tabs 902 and 904 along the circumference of the proximal hub 310a.

In at least some embodiments, the lead-stabilization feature 1102 defines two or more notches 1104 formed in the proximal hub 310a. In at least some embodiments, the number of notches 1104 is equal to the number of splittable regions 906. In at least some embodiments, the lead-stabilization feature 1102 defines two notches 1104 that are formed in the proximal hub 310a 180-degrees apart from one another along the circumference of the proximal hub 310a. In at least some embodiments, the lead-stabilization feature 1102 defines two notches 1104 that are formed in the proximal hub 310a 180-degrees apart from one another and that are each 90-degrees from each of the tabs 902 and 904 along the circumference of the proximal hub 310a.

Figure 12:
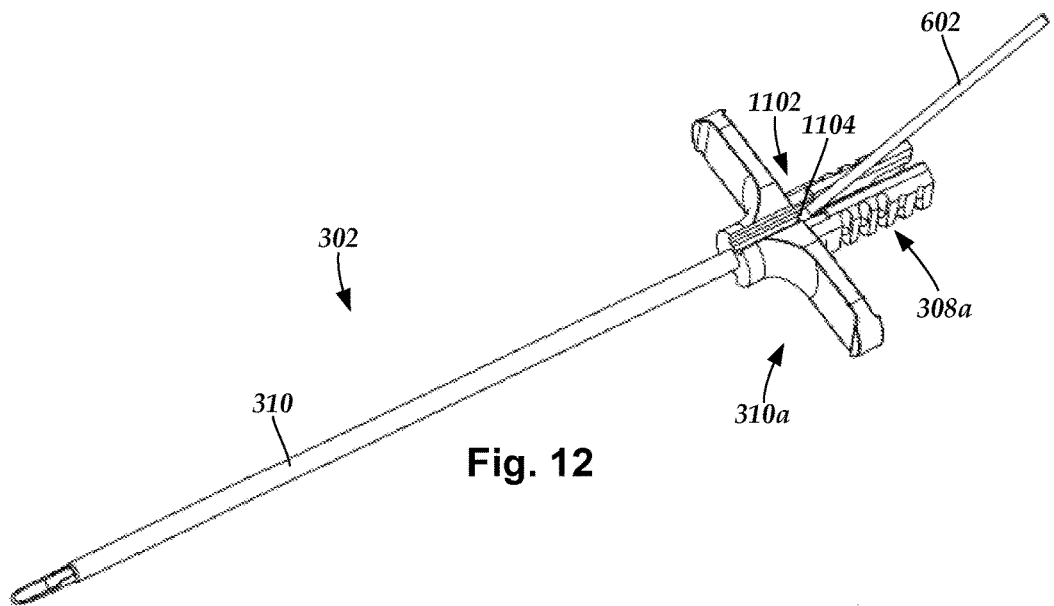
FIG. 12 is a schematic perspective view of one embodiment of the lead of FIG. 6A inserted into the outer insertion needle of FIG. 6A which, in turn, is inserted into the splittable member of FIG. 11, the lead extending through the notch of FIG. 11, according to the invention.
Figure 13:
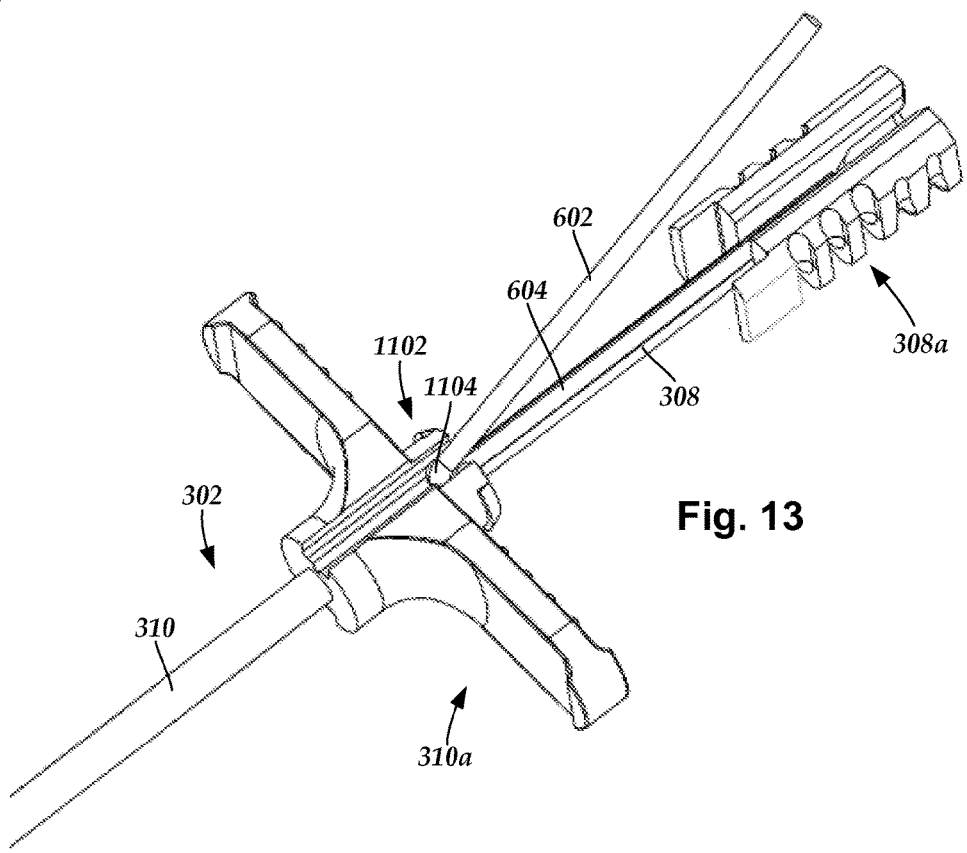
FIG. 13 is a schematic perspective view of one embodiment of the outer insertion needle of FIG. 12 being removed from the splittable member of FIG. 12 and the lead of FIG. 12, while the lead is retained by the notch of FIG. 12 and remains in place during removal of the outer insertion needle, according to the invention.
Figure 14:
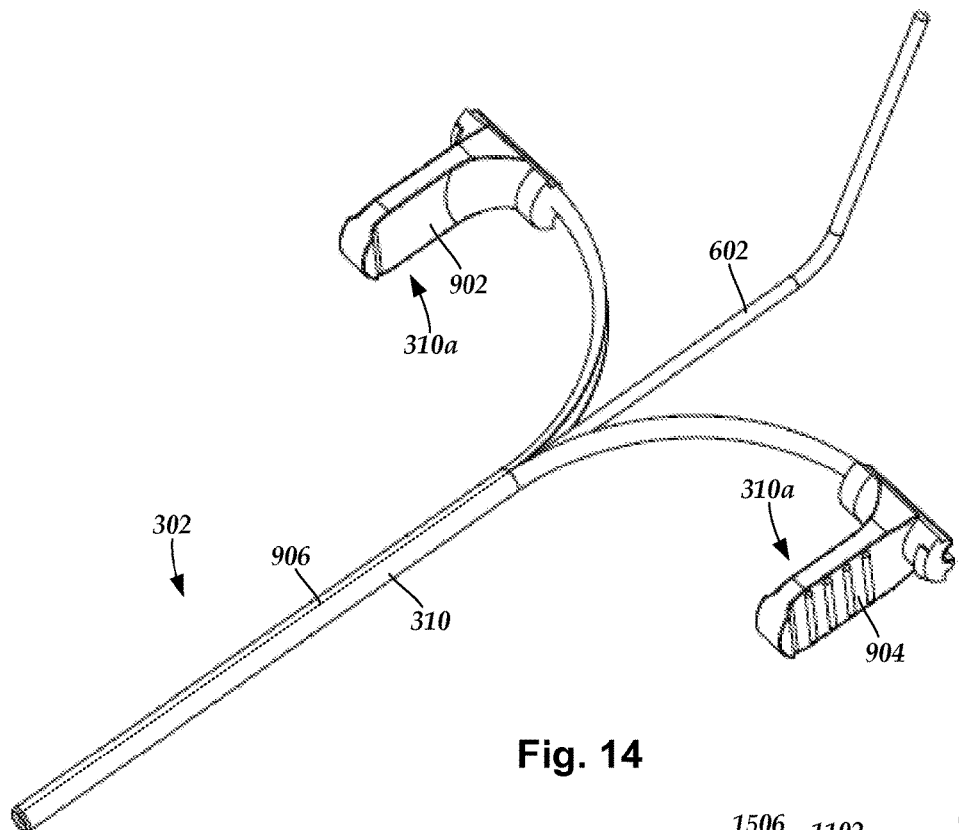
FIG. 14 is a schematic perspective view of one embodiment of the splittable member of FIG. 13 and the lead of FIG. 13 after removal of the outer insertion needle of FIG. 13 with the splittable member being split apart to remove the splittable member from the lead, according to the invention.

FIGS. 12-14 illustrate one embodiment of using the lead-stabilization feature during a lead implantation procedure. FIG. 12 illustrates one embodiment of the lead 602 inserted into the channel 604 (see e.g., FIG. 13) of the outer insertion needle 308 which, in turn, is inserted into the splittable member 310. FIG. 12 shows a portion of the lead 602 extending from the proximal hub 310a inserted into the notch 1104 of the lead-stabilization feature 1102.

FIG. 13 illustrates one embodiment of the lead 602 stabilized by the lead-stabilization feature 1102 while the outer insertion needle 308 is being removed from the splittable member 310 and the lead 602. In at least some embodiments, the lead-stabilization feature 1102 prevents the portion of the lead 602 distal to the notch 1104 from moving relative to the splittable member 310 while the lead 602 is retained by the lead-stabilization feature 1102.

FIG. 14 illustrates one embodiment of the lead 602 and the splittable member 310. The outer insertion needle 308 has been fully removed from the splittable member 310 and the lead 602. The splittable member 310 is shown in FIG. 14 being split apart along the splittable regions 906 to remove the splittable member from the lead 602.

Figure 15:
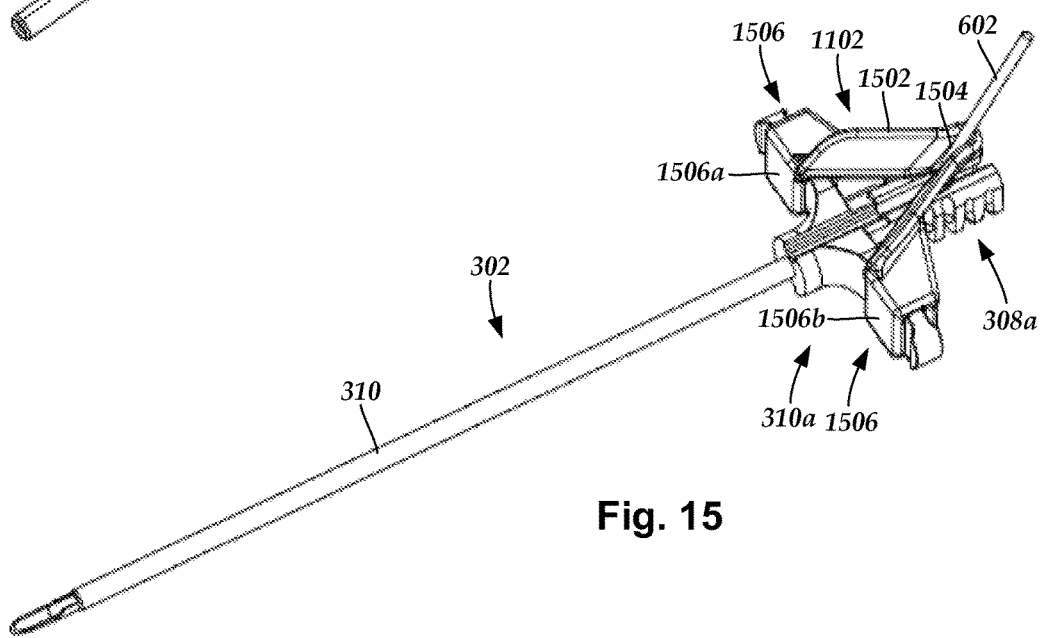
FIG. 15 is a schematic perspective view of a second embodiment of a lead-stabilization feature incorporated into the lead introducer of FIG. 4, the lead-stabilization feature formed as a bracket removably coupled to a proximal hub of a splittable member of the lead introducer, the bracket retaining a portion of a lead inserted into, and extending from, the splittable member, according to the invention.

Turning to FIG. 15, in at least some embodiments the lead-stabilization feature includes a bracket attachable to the lead introducer. The bracket may be removably attachable to the lead introducer. The bracket may be attachable to the splittable member. In at least some embodiments, the bracket is removably attachable to the splittable member. In at least some embodiments, the bracket is attachable to the proximal hub of the splittable member. The lead-stabilization feature may include the bracket in lieu of, or in addition to, the notch.

FIG. 15 illustrates another embodiment of the lead-stabilization feature 1102. In FIG. 15, the lead-stabilization feature 1102 is formed as a bracket 1502 configured and arranged to removably receive a portion of the lead 602 extending from the proximal hub 310a. The bracket 1502 includes a lead-receiving region 1504 and one or more attachment elements 1506. In FIG. 15 two attachment elements 1506a and 1506b are shown. The bracket 1502 can be formed from any suitable material including, for example, plastic. The bracket 1502 can be formed using any suitable technique including, for example, injection molding.

The lead-receiving feature 1102 may releasably receive the lead 602 using in any suitable technique. In at least some embodiments, the lead-receiving feature 1102 is formed as a groove having a diameter that is slightly smaller than a diameter of the lead 602 so that, when the lead 602 is inserted into the groove, the lead 602 forms an interference fit with the groove. In which case, a user may place a portion of the lead 602 extending from the proximal hub 310a into the groove of the lead-receiving feature 1102 prior to removal of the outer insertion needle 308.

The attachment element 1506 may be formed in any suitable manner. In at least some embodiments, the attachment element 1506 is configured and arranged to slidably couple with the lead introducer 302. In at least some embodiments, the attachment element 1506 is configured and arranged to slidably couple with one or more of the tabs 902 and 904 of the splittable member 310. Alternately (or additionally), the attachment element 1506 includes one or more snaps, clips, hasps, or the like, for removably coupling the bracket 1502 to one or more of the tabs 902 and 904 of the splittable member 310.

Alternately, the attachment element 1506 may be configured and arranged for permanent attachment to the splittable member 310. In which case, the lead-stabilization feature 1102 may be configured and arranged to be split apart during, or subsequent to, splitting of the splittable member 310 during removal of the splittable member 310 from the lead 602.

Figure 16:
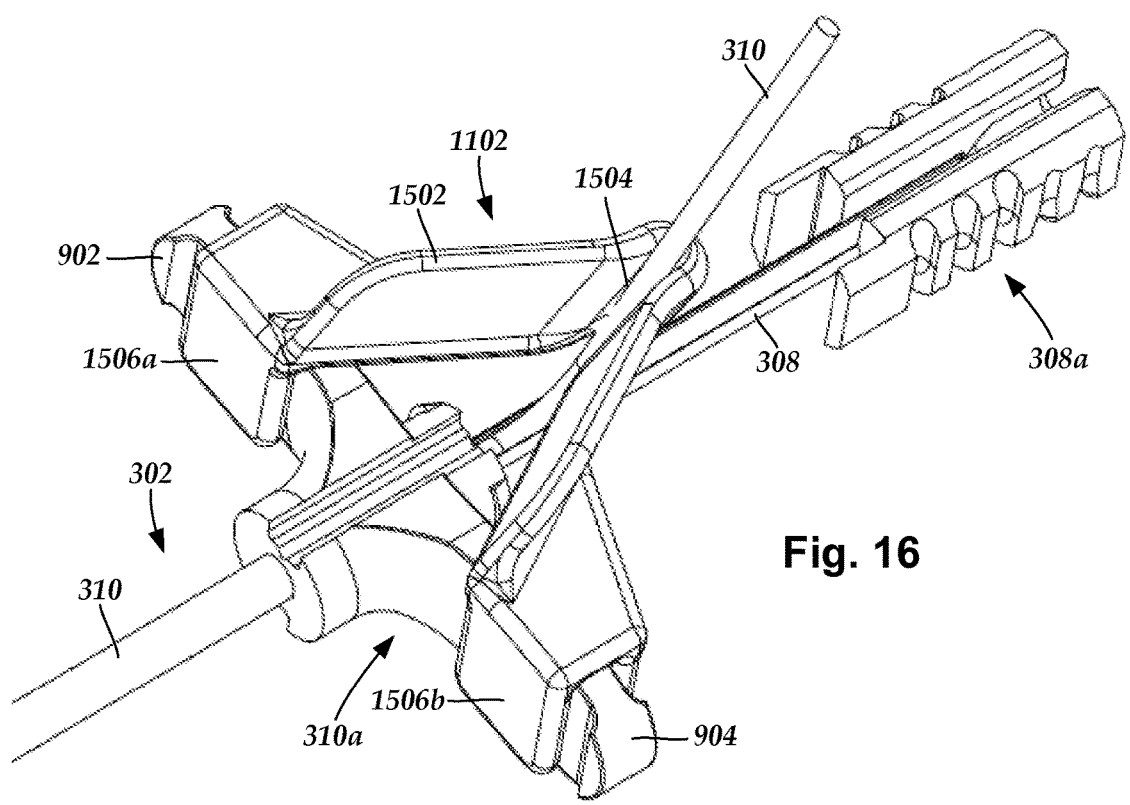
FIG. 16 is a schematic perspective view of one embodiment of an outer insertion needle being removed from the splittable member of FIG. 15 and the lead of FIG. 15, while the lead extends through the bracket of FIG. 15 and remains in place during removal of the outer insertion needle, according to the invention.

FIG. 16 illustrates one embodiment of the lead 602 stabilized by the lead-stabilization feature 1102 while the outer insertion needle 308 is being removed from the splittable member 310. In at least some embodiments, the lead-stabilization feature 1102 prevents the portion of the lead 602 distal to the bracket 1502 from moving relative to the splittable member 310 while the lead 602 is retained by the lead-stabilization feature 1102.

As mentioned above, when the lead 602 is received by the lead-receiving region 1504 the portion of the lead 602 distal to the bracket 1502 does not move relative to the splittable member 310. In which case, it may be advantageous to refrain from coupling the bracket 1502 to the lead introducer 302 during a lead-implantation procedure until after the lead (which is received by the outer insertion needle 308 which, in turn, is received by the splittable member 310) is placed in operational proximity to the target stimulation location.

Figure 17:
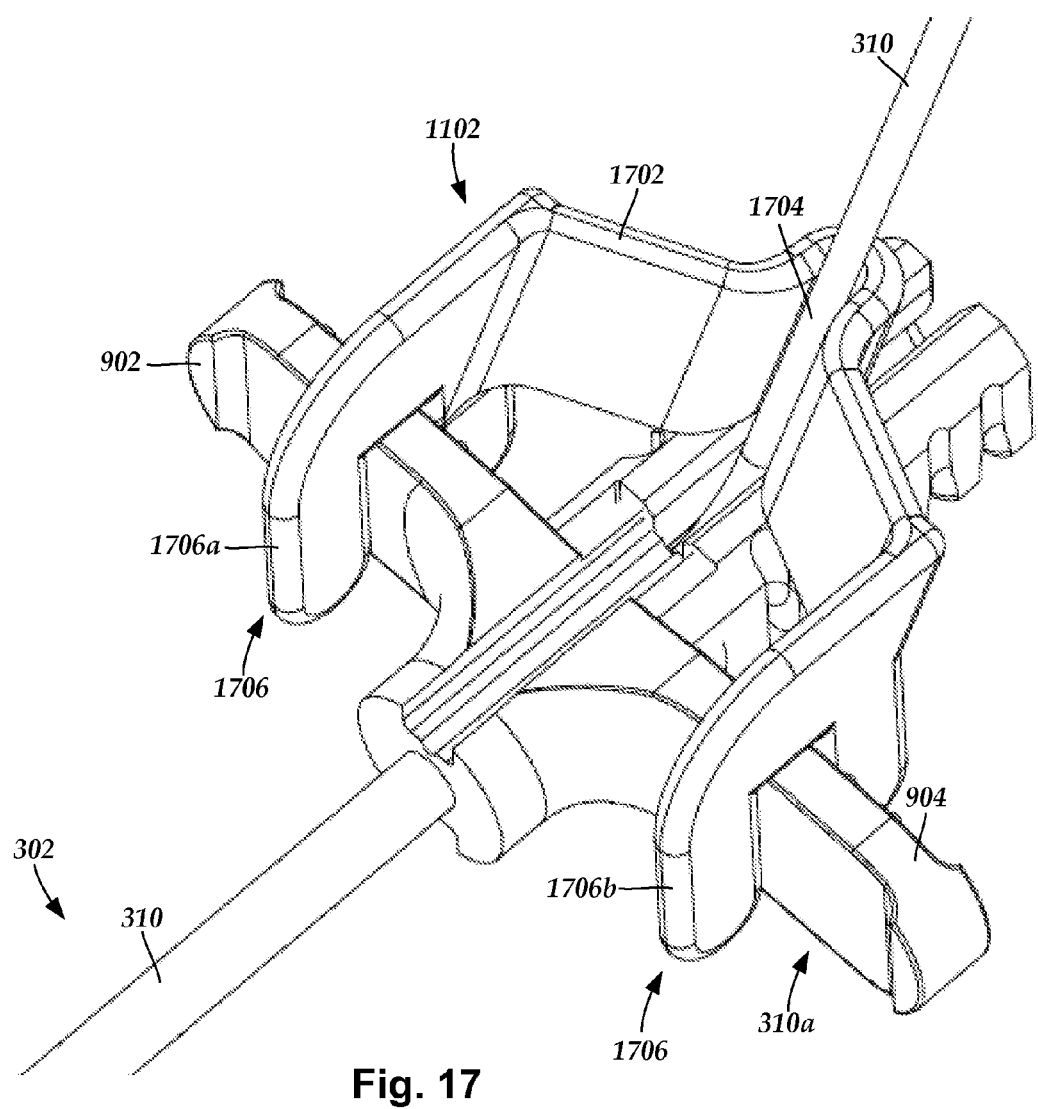
FIG. 17 is a schematic perspective view of a third embodiment of a lead-stabilization feature incorporated into the lead introducer of FIG. 4, the lead-stabilization feature formed as a bracket removably coupled to a proximal hub of a splittable member of the lead introducer, the bracket retaining a portion of a lead inserted into, and extending from, the splittable member, according to the invention.

FIG. 17 illustrates a third embodiment of the lead-stabilization feature 1102. In FIG. 17, the lead-stabilization feature 1102 is formed as a bracket 1702 configured and arranged to removably receive a portion of the lead 602 extending from the proximal hub 310a. The bracket 1702 includes a lead-receiving region 1704 and one or more attachment elements 1706. In FIG. 17 two attachment elements 1706a and 1706b are shown. The bracket 1702 can be formed from any suitable material including, for example, plastic. The bracket 1702 can be formed using any suitable technique including, for example, injection molding.

The lead-receiving feature 1102 shown in FIG. 17 may receive the lead 602 using in any suitable technique. In at least some embodiments, the lead-receiving feature 1102 is formed as a groove having a diameter that is slightly smaller than a diameter of the lead 602 so that, when the lead 602 is inserted into the groove, the lead 602 forms an interference fit with the groove. In which case, a user may place a portion of the lead 602 extending from the proximal hub 310a into the groove of the lead-receiving feature 1102 prior to removal of the outer insertion needle 308.

The attachment element 1706 may be formed in any suitable manner. In at least some embodiments, the attachment element 1706 is configured and arranged to slidably couple with the lead introducer 302. In at least some embodiments, the attachment element 1706 is configured and arranged to slidably couple with one or more of the tabs 902 and 904 of the splittable member 310. Alternately (or additionally), the attachment element 1706 includes one or more snaps, clips, hasps, or the like, for removably coupling the bracket 1702 to one or more of the tabs 902 and 904 of the splittable member 310.

It will be understood that the above-described lead-stabilization feature may find use with other medical devices besides lead introducers for electrical stimulation systems. The above-described lead-stabilization feature may be used, for example, with catheter systems, such as catheters that are inserted into patients (e.g., using the Seldinger technique, or the like).

Figure 18:
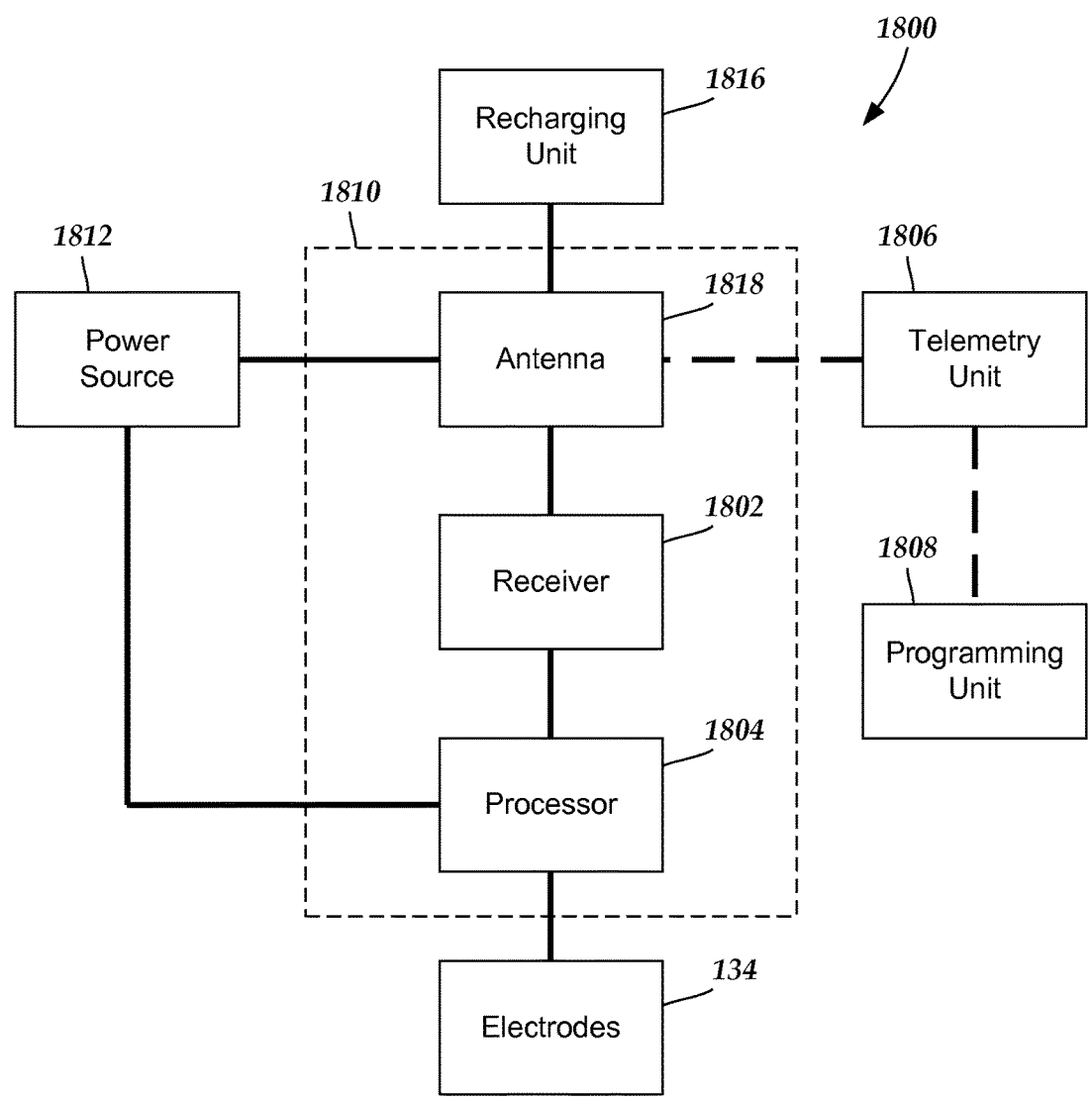
FIG. 18 is a schematic overview of one embodiment of components of a stimulation system, including an electronic subassembly disposed within a control module, according to the invention.

FIG. 18 is a schematic overview of one embodiment of components of an electrical stimulation system 1800 including an electronic subassembly 1810 disposed within a control module. It will be understood that the electrical stimulation system can include more, fewer, or different components and can have a variety of different configurations including those configurations disclosed in the stimulator references cited herein.

Some of the components (for example, a power source 1812, an antenna 1818, a receiver 1802, and a processor 1804) of the electrical stimulation system can be positioned on one or more circuit boards or similar carriers within a sealed housing of an implantable pulse generator, if desired. Any power source 1812 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 1818 or a secondary antenna. The external power source can be in a device that is mounted on the skin of the user or in a unit that is provided near the user on a permanent or periodic basis.

If the power source 1812 is a rechargeable battery, the battery may be recharged using the optional antenna 1818, if desired. Power can be provided to the battery for recharging by inductively coupling the battery through the antenna to a recharging unit 1816 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 1804 is generally included to control the timing and electrical characteristics of the electrical stimulation system. For example, the processor 1804 can, if desired, control one or more of the timing, frequency, strength, duration, and waveform of the pulses. In addition, the processor 1804 can select which electrodes can be used to provide stimulation, if desired. In some embodiments, the processor 1804 selects which electrode(s) are cathodes and which electrode(s) are anodes. In some embodiments, the processor 1804 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1808 that, for example, allows modification of pulse characteristics. In the illustrated embodiment, the processor 1804 is coupled to a receiver 1802 which, in turn, is coupled to the optional antenna 1818. This allows the processor 1804 to receive instructions from an external source to, for example, direct the pulse characteristics and the selection of electrodes, if desired.

In one embodiment, the antenna 1818 is capable of receiving signals (e.g., RF signals) from an external telemetry unit 1806 which is programmed by the programming unit 1808. The programming unit 1808 can be external to, or part of, the telemetry unit 1806. The telemetry unit 1806 can be a device that is worn on the skin of the user or can be carried by the user and can have a form similar to a pager, cellular phone, or remote control, if desired. As another alternative, the telemetry unit 1806 may not be worn or carried by the user but may only be available at a home station or at a clinician's office. The programming unit 1808 can be any unit that can provide information to the telemetry unit 1806 for transmission to the electrical stimulation system 1800. The programming unit 1808 can be part of the telemetry unit 1806 or can provide signals or information to the telemetry unit 1806 via a wireless or wired connection. One example of a suitable programming unit is a computer operated by the user or clinician to send signals to the telemetry unit 1806.

The signals sent to the processor 1804 via the antenna 1818 and the receiver 1802 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1800 to cease operation, to start operation, to start charging the battery, or to stop charging the battery. In other embodiments, the stimulation system does not include the antenna 1818 or receiver 1802 and the processor 1804 operates as programmed.

Optionally, the electrical stimulation system 1800 may include a transmitter (not shown) coupled to the processor 1804 and the antenna 1818 for transmitting signals back to the telemetry unit 1806 or another unit capable of receiving the signals. For example, the electrical stimulation system 1800 may transmit signals indicating whether the electrical stimulation system 1800 is operating properly or not or indicating when the battery needs to be charged or the level of charge remaining in the battery. The processor 1804 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead introducer comprising:
    an insertion-needle assembly configured and arranged for receiving an electrical stimulation lead, the insertion-needle assembly having a proximal end, a distal end, and a longitudinal length extending from the proximal end to the distal end, the insertion-needle assembly comprising an outer insertion needle having a proximal end, a distal end, and a longitudinal length extending from the proximal end to the distal end;
    a splittable member having a proximal end, a distal end, and a longitudinal length extending from the proximal end to the distal end, the splittable member comprising a proximal hub disposed at the proximal end, the splittable member defining a lumen configured and arranged for receiving at least a portion of the insertion-needle assembly, the splittable member comprising
        at least two pull-apart tabs disposed on the proximal hub of the splittable member, and
        at least one splittable region extending along at least a portion of the longitudinal length of the splittable member from between the at least two pull-apart tabs, the at least one splittable region configured and arranged for separating when the at least two pull-apart tabs are pulled apart from one another in directions approximately orthogonal to the splittable member; and
    a lead-stabilization feature disposed on or attachable to the splittable member, configured and arranged for receiving, and temporarily retaining, a portion of an electrical stimulation lead extending outward from the splittable member such that the lead does not move relative to the splittable member when the lead is received by the lead-stabilization feature and the outer insertion needle is being removed from the lead, wherein the lead-stabilization feature comprises a notch defined along the proximal hub of the splittable member, the notch configured and arranged to form an interference fit with a portion of the electrical stimulation lead extending outwardly from the proximal hub of the splittable member when the electrical stimulation lead is inserted into the lumen of the splittable member.

2. The lead introducer of claim 1, wherein the notch is continuous with the lumen of the splittable member.

3. The lead introducer of claim 1, wherein the at least one splittable region extends through the notch.

4. The lead introducer of claim 1, wherein the notch is a first notch, and wherein the lead-stabilization feature further comprises a second notch.

5. The lead introducer of claim 4, wherein the at least one splittable region comprises a first splittable region and a second splittable region, and wherein the first splittable region extends through the first notch and the second splittable region extends through the second notch.

6. The lead introducer of claim 1, wherein the lead-stabilization feature comprises each of the notch defined along the proximal hub of the splittable member and a bracket removably coupleable to the splittable member.

7. A lead introducer comprising:
an insertion-needle assembly configured and arranged for receiving an electrical stimulation lead, the insertion-needle assembly having a proximal end, a distal end, and a longitudinal length extending from the proximal end to the distal end, the insertion-needle assembly comprising an outer insertion needle having a proximal end, a distal end, and a longitudinal length extending from the proximal end to the distal end;
a splittable member having a proximal end, a distal end, and a longitudinal length extending from the proximal end to the distal end, the splittable member comprising a proximal hub disposed at the proximal end, the splittable member defining a lumen configured and arranged for receiving at least a portion of the insertion-needle assembly, the splittable member comprising
at least two pull-apart tabs disposed on the proximal hub of the splittable member, and
at least one splittable region extending along at least a portion of the longitudinal length of the splittable member from between the at least two pull-apart tabs, the at least one splittable region configured and arranged for separating when the at least two pull-apart tabs are pulled apart from one another in directions approximately orthogonal to the splittable member; and
a lead-stabilization feature disposed on or attachable to the splittable member, configured and arranged for receiving, and temporarily retaining, a portion of an electrical stimulation lead extending outward from the splittable member such that the lead does not move relative to the splittable member when the lead is received by the lead-stabilization feature and the outer insertion needle is being removed from the lead, wherein the lead-stabilization feature comprises a bracket removably coupleable to the splittable member and separate from the outer insertion needle.

8. The lead introducer of claim 7, wherein the bracket is removably coupleable to at least one of the at least two pull-apart tabs of the splittable member.

9. The lead introducer of claim 7, wherein the bracket is removably coupleable to each of the at least two pull-apart tabs of the splittable member.

10. The lead introducer of claim 7, wherein the bracket comprises a groove configured and arranged to form an interference fit with the electrical stimulation lead.

11. The lead introducer of claim 7, wherein the groove is aligned radially with the at least one splittable region when the bracket is coupled to the splittable member.

12. An insertion kit comprising:
the lead introducer of claim 1; and
an electrical stimulation lead configured and arranged for insertion into the lead introducer during a lead-implantation procedure, the electrical stimulation lead comprising
a lead body having a distal end portion and a proximal end portion,
a plurality of electrodes disposed along the distal end portion of the lead body,
a plurality of terminals disposed along the proximal end portion of the lead body, and
a plurality of conductive wires coupling the plurality of electrodes electrically to the plurality of terminals;
wherein the lead-stabilization feature of the lead introducer is configured and arranged for receiving, and temporarily retaining, a portion of the electrical stimulation lead extending outward from the splittable member of the lead introducer such that the electrical stimulation lead does not move relative to the splittable member when the electrical stimulation lead is received by the lead-stabilization feature.

13. An electrical stimulation system comprising:
the insertion kit of claim 12;
a control module configured and arranged to electrically couple to the proximal end portion of the lead body, the control module comprising
a housing, and
an electronic subassembly disposed in the housing; and
a connector for receiving the electrical stimulation lead, the connector comprising
a connector housing defining a port for receiving the proximal end portion of the lead body, and
a plurality of connector contacts disposed in the connector housing, the plurality of connector contacts configured and arranged to couple to the plurality of terminal disposed along the proximal end portion of the lead body.

14. A method for implanting an electrical stimulation lead into a patient, the method comprising:
providing the lead introducer of claim 1;
disposing the insertion-needle assembly of the lead introducer at least partially into the splittable member of the lead introducer;
guiding the splittable member and the insertion-needle assembly to a position within the patient;
removing a first element of the insertion-needle assembly from the patient, leaving the outer insertion needle of the insertion-needle assembly disposed in the splittable member;
inserting a distal end portion of an electrical stimulation lead into the splittable member subsequent to removing the first element of the insertion-needle assembly from the patient, the electrical stimulation lead comprising a plurality of electrodes disposed along the distal end portion of the electrical stimulation lead;
inserting a portion of the electrical stimulation lead extending from the splittable member into the lead-stabilization feature of the lead introducer, the lead-stabilization feature preventing the distal end portion of the electrical stimulation lead from moving relative to the splittable member when the electrical stimulation lead is received by the lead-stabilization feature;
removing the outer insertion needle of the insertion-needle assembly from the patient while the electrical stimulation lead is received by the lead-stabilization feature;
removing the electrical stimulation lead from the lead-stabilization feature after the outer insertion needle of the insertion-needle assembly is removed from the patient; and removing the splittable member from the patient, leaving the distal end portion of the electrical stimulation lead implanted in the patient at a target stimulation location.

15. The method of claim 14, wherein inserting a portion of the electrical stimulation lead extending from the splittable member into the lead-stabilization feature comprises forming an interference fit between the electrical stimulation lead and the lead-stabilization feature.

16. The method of claim 14, wherein inserting a portion of the electrical stimulation lead extending from the splittable member into the lead-stabilization feature comprises inserting the electrical stimulation lead into a notch formed along the proximal hub of the splittable member.

17. The method of claim 14, wherein inserting, a portion of the electrical stimulation lead extending from the splittable member into the lead-stabilization feature comprises inserting the electrical stimulation lead into a bracket removably coupled to the splittable member.

18. The method of claim 17, further comprising coupling the bracket to the splittable member prior to removing the outer insertion needle of the insertion-needle assembly from the patient.

19. The method of claim 17, further comprising removing the bracket from the splittable member prior to separating the splittable member into at least two parts.

* * * * *